United States Patent [19]
Lebaut et al.

[11] Patent Number: 5,965,582
[45] Date of Patent: Oct. 12, 1999

[54] N-BENZYLINDOLE AND BENZOPYRAZOLE DERIVATIVES WITH ANTI-ASTHMATIC, ANTI-ALLERGIC, ANTI-INFLAMMATORY AND IMMUNEMODULATING EFFECT

[75] Inventors: Guillaume Lebaut, Saint-Sebastien; Fabienne Fouchard, Nantes, both of France; Bernhard Kutscher, Maintal, Germany; Peter Emig, Niederdorfelden, Germany; Ilona Fleischhauer, Offenbach, Germany; Jürgen Schmidt, Gründau, Germany; Stefan Szelenyi, Schwaig, Germany

[73] Assignee: ASTA Medica Aktiengesellschaft, Dresden, Germany

[21] Appl. No.: 08/776,616

[22] PCT Filed: Jul. 20, 1995

[86] PCT No.: PCT/EP95/02867

§ 371 Date: May 12, 1997

§ 102(e) Date: May 12, 1997

[87] PCT Pub. No.: WO96/04266

PCT Pub. Date: Feb. 15, 1996

[30] Foreign Application Priority Data

Aug. 3, 1994 [DE] Germany .............................. 44 27 393
Mar. 31, 1995 [DE] Germany ........................... 195 11 916

[51] Int. Cl.$^6$ ........................ A61K 31/44; C07D 209/22
[52] U.S. Cl. .................. 514/338; 546/277.7; 546/277.4; 546/111; 546/119; 546/113; 546/139; 546/152; 546/275.7; 544/333; 544/362; 544/373; 548/360.1; 548/452; 514/256; 514/272; 514/253; 514/292; 514/303; 514/300; 514/307; 514/314; 514/339; 514/415
[58] Field of Search .............................. 546/277.7, 277.4; 514/338

[56] References Cited

U.S. PATENT DOCUMENTS

| | | | |
|---|---|---|---|
| Re. 33,833 | 2/1992 | Janssens et al. | 546/118 |
| 3,182,071 | 5/1965 | Shauel | 546/277.4 |
| 3,445,472 | 5/1969 | Archibald | 546/277.7 |
| 3,453,366 | 7/1969 | Mauvernay et al. | 514/253 |
| 3,470,194 | 9/1969 | Palazza . | |
| 3,527,761 | 9/1970 | Archibald et al. | 546/277.4 |
| 3,547,922 | 12/1970 | Archer . | |
| 3,953,442 | 4/1976 | Demarne | 546/277.4 |
| 4,350,634 | 9/1982 | Stadler . | |
| 4,359,468 | 11/1982 | Freter et al. | 546/199 |
| 4,556,660 | 12/1985 | Janssens et al. | 514/272 |
| 4,743,609 | 5/1988 | Hosoi et al. | 546/277.7 |
| 4,760,074 | 7/1988 | Janssens et al. | 514/303 |
| 4,820,822 | 4/1989 | Janssens et al. | 546/118 |
| 5,236,921 | 8/1993 | Emonds-Ai et al. | 514/252 |
| 5,317,025 | 5/1994 | Bru-Magniez et al. | 514/323 |
| 5,350,852 | 9/1994 | Emonds-Alt et al. | 544/336 |

FOREIGN PATENT DOCUMENTS

| | | |
|---|---|---|
| 0 326 331 | 8/1989 | European Pat. Off. . |
| 0 340 010 | 11/1989 | European Pat. Off. . |
| 3004700 | 8/1980 | Germany . |
| 944443 | 12/1963 | United Kingdom . |
| 92/06973 | 4/1992 | WIPO . |
| 93/11106 | 6/1993 | WIPO . |
| 93/21180 | 10/1993 | WIPO . |
| 94/26736 | 11/1994 | WIPO . |
| 95/16684 | 6/1995 | WIPO . |
| 96/04266 | 2/1996 | WIPO . |

OTHER PUBLICATIONS

Sokolova et al., N–(4–Pyrimidyl)Ethylamine Derivatives, Khimiya Geterotsiklicheskikh Soedinenii, vol. 4, No. 2, pp. 343–347, 1968.

Walker et al., "3–Aminomethylindoles and 2–(3–Indoyl)oxazolidines from indole–3–aldimines. Some Observations on the Acetylation of Schiff Bases," Jour. Org. Chem. vol. 26, (1961), pp. 432–439.

Chi–Ting et al., "Synthesis of Some N–Phenylpiperazine Derivatives as Potential Central Depressants," ACTA Pharmaceutica Sinica, vol. XI, No. 10, (1964) pp. 693–699.

DeGraw et al, "5–Nitro– and 5–Aminogramines", Journal of Medicinal Chemistry, vol. 9, No. 1 (1966) pp. 140–142.

Jain et al., "Chemical and Pharmacological Investigations of Some ω–Substituted Alkylamino–3–aminopyridines," Journal of Medicinal Chemistry, vol. II, (1968) pp. 87–92.

Avon–Samuel, "3–Aminoacetylindoles," "27–Heterocyclic Compounds,"No. 871526b, Chemical Abstracts, vol. 68, (1968) pp. 8399–8400.

Nakahishi et al., "Indoles," No. 112805p, "27–Heterocyclic Compounds", Chemical Abstracts, vol. 71, (1969) p. 365.

Suvorov et al., "Indoles from phenylhydrazones" No. 66814m, "27–Heterocyclic Compounds", Chemical Abstracts, vol. 72 (1970) p. 383.

Yamamoto et al., "Indoles," No. 77048, "27–Heterocyclic Compounds", Chemical Abstracts, vol. 73, (1970) p. 353.

Singh et al., "Antimalarials. 7–Chloro–4–(substituted amino) Quinolines", Journal of Medicinal Chemistry, vol. 14, No. 4 (1971) pp. 283–286.

Boch et al., "Indole pharmaceuticals," No. 108368s, Chemical Abstracts, vol. 80 (1974) p. 404.

(List continued on next page.)

*Primary Examiner*—Donald G. Daus
*Attorney, Agent, or Firm*—Pillsbury Madison & Sutro LLP

[57] ABSTRACT

The N-benzylindole- and benzopyrazole derivatives of the general formula 1

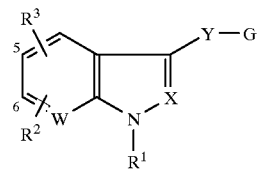

Formula 1 possess anti-asthmatic, anti-allergic, anti-inflammatory and immunomodulating effect and are suitable for the preparation of medicaments.

17 Claims, No Drawings

OTHER PUBLICATIONS

Johnson et al., "Synthesis and pharmacological examination of 1–(3–methoxy–4–methylpheny)–2–aminoprppane . . . ," No. 228483t, "25–Benzenes", Chemical Abstracts, vol. 114 (1991) p. 793.

Macor et al., "Synthesis and Serotonergic Pharmacology of the Enantiomers of . . . ", Journal of Medicinal Chemistry, vol. 35, No. 23 (1992) pp. 4503–4505.

Ezer et al., "Process for producing new tetrahydropyrido[3,4–b]indole derivatives as ulcer inhibitors", No. 54535t, "28–Hetercycles", Chemical Abstracts, vol. 120 (1994) p. 981.

Sato et al., "3–Aminoacetylindoles," Chemical Abstracts, No. 25292s, vol. 73 (1970), p. 349.

Biniecki et al., "Synthesis of 3–Indolylacetylpiperazines and Reduction of Compounds Obtained with Lithium Aluminum Hydride", Annales Societatis Chimicae Polonorum, vol. 49 (1975) pp. 1585–1587.

Germain et al., "Synthèses d'inoles par cyclisation réductrice. II. (1) Nouvelle méthode de synthèse des indole carboxamides–3, donnant äcces aux dérivés de la gramine", Journal of Heterocyclic Chemistry, vol. 13, No. 6 (1976); pp. 1209–1218.

Alemany Soto et al., "3–(2–Aminoethyl)indole derivatives", No. 106380q, "27–Heterocycles", Chemical Abstracts, vol. 86 (1977) p. 491.

Chodkowski et al., "Synthesis of Some Amides of 1–Butyl–4–Phenyl–Piperidine–4–Carboxylic and 3–Indolylacetic Acids", Annales Societatis Chimicae Plonorum, vol. 51 (1977) pp. 1231–1234.

Glennon, R. A., "Serotonin Receptor Binding Affinities of Tryptamine Analogues", Journal of Medicinal Chemistry, vol. 22, No. 4 (1979) pp. 428–432.

Kubo et al., "Tryptamine derivatives", No. 30565w, Chemical Abstracts, vol. 94 (1981), p. 554.

Verma et al., "Indolyl Compounds as Antiinflammatory Agents", Arch. Pharm. vol. 315, No. 4 (1982) pp. 358–363.

El–Gendy et al., "Synthesis of 3–Indoleacetyl Derivatives of Certain Amino and Phenolic Compounds Likely to Possess Antiinflammatory Activity", Pharmazie 37, H. 7 (1982) pp. 481–482, 475.

Zelesko et al., "Cardiac–Slowing Amidines Containing the 3–Thioindole Group. Potential Antianginal Agents", Journal of Medicinal Chemistry. vol. 26, No. 2 (1983) pp. 230–237.

Marumo et al., "Preparation of Indoleacetic acid derivative as plant growth regulators", No. 134195d, "27–Heterocycles", Chemical Abstracts, vol. 107 (1987) pp. 711–712.

Marumo et al., Indolescetc acid derivatives as plant grouth regulators and their preparation, No. 7220r, "27–Heterocycles", Chemical Abstracts, vol. 111 (1989) p. 7226.

Singh et al., "Preparation of di–(D–tryptophyl and/or tetrahydropyridoindolylcarbonyl)–containging peptide . . . ", No. 7935y, Chemical Abstracts, vol. 112 (1990) p. 780.

N-BENZYLINDOLE AND BENZOPYRAZOLE DERIVATIVES WITH ANTI-ASTHMATIC, ANTI-ALLERGIC, ANTI-INFLAMMATORY AND IMMUNEMODULATING EFFECT

BACKGROUND OF THE INVENTION

1. Field of the Invention

The invention relates to N-benzylindole- and benzopyrazole derivatives having anti-asthmatic, anti-allergic, anti-inflammatory and immunomodulating effects.

2. Background Information

Indole derivatives have many uses as synthetic building blocks for the synthesis of drugs, for example the drugs indomethacin and acemethacin have an N-substituted indole skeleton.

Indomethacin is the prototype of compounds having a predominantly anti-inflammatory and anti-rheumatic effect.

An indazole derivative that can be cited is the substance bendazac which has an anti-inflammatory effect; the synthesis of the substance, IUPAC name [(1-benzyl-1H-indazole-3-yl)oxy]acetic acid, is described in US PS 3 470 194.

DE-OS 42 25 756 and EP 392 317 describe benzimidazoles which constitute angiotensin antagonists, in particular angioterlsin-II antagonists.

DE-OS 27 31 647 describes 1,3-benzothiolanes and their pharmaceutically useful salts.

Colantti (Chim. Ther 6(5), 367–79) describe indole derivatives which have coccidiostatic properties.

Clark et al (J. Med. Chem, 36 (18), 264-57) describe 1H-indole-3-carboxamides substituted by quinuclidyl radicals and derivatives at the acid amide nitrogen. These compounds are $5HT_3$ antagonists and can, for example, be used as anti-emetics.

EP 490 263 describes N-methyl-indole derivatives as 5-HT-antagonists.

EP 485 962 describes N-methyl-indole derivatives as $S_3$-receptor antagonists.

WO 88/5432 describes N-alkyl substituted 3-indolecarboxylic acid derivatives as diuretics and cardiovascularly active substances.

WO 93/2062 also describes N-alkyl-substituted 3-indole carboxylic acid amides, in which the amide nitrogen is substituted by a heterocyclic system, such as a tetrazole ring or a substituted tetrazole ring.

EP 580 502 describes 3-(hydroxybenzylidenyl)-indoline-2-one-derivatives with an anti-inflammatory, analgesic, anti-arteriosclerotic and anti-asthmatic effect. The compounds, which can be present as an E/Z-isomer mixture, inhibit $LTB_4$ synthesis.

The compounds carry various substituents at the indoline nitrogen; there is a keto- or thioketo group at the 2-carbon atom of the indoline ring.

SUMMARY OF THE INVENTION

It is the object of the invention to provide novel compounds which have an anti-asthmatic, anti-allergic, anti-inflammatory and immunemodulating effect; processes are also described for the preparation of the compounds and of drugs that can be obtained from the compounds.

The object of the invention therefore comprises compounds of the general formula 1

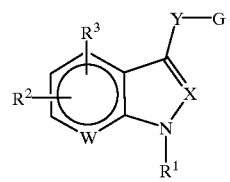

Formula 1 having the following meanings:

$R^1$=hydrogen, $(C_1-C_6)$alkyl, where the alkyl group can be straight-chained or branched and can be substituted once or several times by halogen, phenyl, which for its part can be substituted once or several times by halogen, $(C_1-C_6)$alkyl, $(C_3-C_7)$cycloalkyl, carboxyl groups, esterified carboxyl groups, trifluoromethyl groups, trichloromethyl groups, hydroxyl groups, methoxy groups, ethoxy groups, benzyloxy groups, benzyl groups or benzoyl groups, 2- or 3-thienyl, 2-quinolyl, 2-, 3- or 4-pyridyl which, for its part, can be substituted once or several times by halogen, $(C_1-C_4)$ alkyl groups or $(C_1-C_4)$alkoxy groups, $(C_3-C_7)$ cycloalkyl, aryl, for example phenyl or naphthyl, heteroaryl, for example 2-, 3- or 4-pyridyl, 2- or 8-quinolyl, 2-thienyl or 1,3 or 8 isoquinolyl, where aryl or heteroaryl can be substituted once or several times by halogen, $(C_1-C_4)$alkyl, $(C_1-C_4)$alkoxy, hydroxy, thiol groups, thioether groups $(C_1-C_4)$alkanoyl groups, CN, —COOH, —$CF_3$, $NO_2$, $(C_1-C_3)$alkoxycarbonyl, an amino group of the general formula

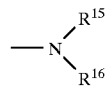

or aroyl, with aryl in the meaning stated.

$R^2$ and $R^3$ can be the same or different and can represent hydrogen, $(C_1-C_6)$alkyl, straight-chained or branched, $(C_3-C_7)$cycloalkyl, $(C_1-C_6)$alkanoyl, $(C_1-C_6)$alkoxy, halogen, benzyloxy, hydroxy, in addition $R^2$ and $R^3$ can represent the nitro group, the amino group, which can be substituted as herein before described, the methoxy group and carbamic acid esters, which are linked to the aromatic ringsystem by the N-atom, W can represent CH or N, Y can represent O, S or a single bond in such a manner that the heterocyclic system is directly associated with the group

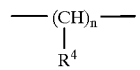

X can represent CH or N, furthermore, when Y stands for a single bond in such a way that the heterocyclic system is directly associated with the group $$—(CH)_n—$$
$$|$$
$$R^4$$

X can represent a >C= group, where a single bond from the group >C=, which is only saturated by one hydrogen atom in formula 1, is now linked via a methylene group to the nitrogen atom of the group $NR^6R^7$ of $R^5$, and where furthermore, if $R^6$ and $R^7$ are equal with hydrogen, this hydrogen is replaced G can be (i)=

$$—(CH)_n—(C)_m—R^5$$
$$\quad\quad |\quad\quad\quad ||$$
$$\quad\quad R^4\quad\quad Z$$

or (ii)=

$$R^{12}\underset{\underset{o}{\diagdown}}{\diagup}\underset{N}{\overset{R^{13}}{\diagup}}—R^{11}$$

or (iii)=$R^{14}$ where, in the case of G=(i)

$R^4$=hydrogen, $(C_1-C_6)$alkyl, where the alkyl group can be straight-chained or branched, $(C_3-C_7)$cycloalkyl, n=1–6 m=0 or 1

$$—(CH)_n$$
$$|$$
$$R^4$$

$R^5$ can represent N-$(C_1-C_6)$alkyl-2-pyrrolidinyl or the radical $$\quad\quad R^6$$
$$\quad\quad /$$
$$—N$$
$$\quad\quad \backslash$$
$$\quad\quad R^7$$

where $R^6$ and $R^7$ can be the same or different and can either represent H, $(C_1-C_6)$alkyl, quinolyl, phenyl which can be substituted with pyridylmethyl or the pyridine skeleton, where the pyridine can optionally be linked to one of the ring carbon atoms and be substituted with the radicals $R^8$ and $R^9$ which can be the same or different and as substituents $R^8$ and $R^9$ can have the the meaning $(C_1-C_6)$alkyl, where the alkyl group can be straight-chained or branched, $(C_3-C_7)$cycloalkyl, $(C_1-C_6)$alkoxy, $NO_2$, NH2, ethoxycarbonylamino or phenoxycarbonylamino, In addition, $R^6{}_1$, $R^7$ and the N-atom to which they are link, can form a piperazine ring-system of formula 2

Formula 2

$$—N\underset{\diagdown\diagup}{\overset{\diagup\diagdown}{}}N—R^{10}$$

where $R^{10}$ can represent the groups $(C_1-C_6)$alkyl, where the alkyl group can be straight-chained or branched, $(C_3-C_7)$cycloalkyl, and phenyl which can be substituted with alkyl, alkoxy, halogen, the benzylhydryl and the bis-F-benzylhydryl group, furthermore $R^5$ can represent a 2-, or 4-pyrimidinylamino ring, which can be substituted several times with a methyl group or a 4-piperidylamino ring, where the N-atom of the piperidine ring can be substituted in each case with H, $(C_1-C_6)$alkyl, where the alkyl group can be straight-chained or branched, $(C_3-C_7)$cycloalkyl, aralkyl, phenyl or the pyridine ring substituted with the groups $NH_2$, $NO_2$, $OCH_3$ and NHCOOEt, $R^5$ also represents the 3- or 4-tetrahydropyridylamino ring, the N-atom of which can be substituted by H, $(C_1-C_6)$alkyl, where the alkyl group can be straight-chained or branched, $(C_3-C_7)$cycloalkyl and aralkyl, Z can represent O or S or two hydrogen atoms for G=(ii)

$R^{11}$ can have the same meaning as $R^1$, $R^{12}$ and $R^{13}$ can be the same or different and independently of one another occupy all the carbon positions at the (non-aromatic) heterocyclic system and have the meaning given above for $R^1$ and o can be 1-4 for G=(iii)

$R^{14}$ can represent benzyl that can be substituted once or several times by halogen, $(C_1-C_6)$-alkyl, where the alkyl group can be straight-chained or branched, $(C_1-C_6)$alkoxy or benzyloxy, or the group $$\quad\quad\quad O$$
$$\quad\quad\quad ||$$
$$—CH_2—C—R^{15}$$

where $R^{15}$ can be hydroxy, 2,3- or 4-pyridylamino, that can be substituted with an amino, nitro $(C_1-C_4)$ alkoxycarbonyl or $(C_1-C_4)$alkoxy-carbonylamino, 4-quinolylamino, that can be substituted with $(C_1-C_4)$alkyl or 2-pyridylmethoxy.

The compounds of the invention can also be present as acid addition salts, for example as salts of mineral acids such as hydrochloric acid, sulfuric acid, phosphoric acid, salts of organic acids, such as acetic acid, lactic acid, malonic acid, maleic acid, fumaric acid, glucuronic acid, citric acid, gluconic acid, embonic acid, methan-sulfonicacid, trifluoracetic acid.

The designation "straight-chained alkyl group" is understood to mean for example radicals such as methyl, ethyl, n-propyl, n-butyl, n-pentyl, n-hexyl, "branched alkyl group" is understood to mean radicals such as isopropyl or tert.-butyl. The designation "alkyl groups" is understood to mean both "straight-chained" and also "branched" alkyl groups. "Cycloalkyl" is understood to mean radicals such as cyclopropyl, cyclobutyl, cyclopentyl, cyclohexyl or cycloheptyl. The designation halogen stands for fluorine, chlorine, bromide or iodine. The designation "alkoxy group" constitutes radicals such as methoxy, ethoxy, propoxy, butoxy, isoproloxy, isobutoxy or pentoxy.

DETAILED DESCRIPTION OF THE INVENTION

The compounds of the invention display a good effect in pharmacological models for the release of histamine according to the following instructions:

Inhibition of allergically-induced histamine release in-vitro (CHIR)

The method described herein below was carried out after Jasani & Stanworth, 1979, J. Immunol. Meth. 30, 55. Sprague-Dawley rats were sensitised against egg albumin (EA) by subcutaneous injection of 30 mg EA with killed Bordetella pertussis bacteria as adjuvant. Four weeks later, the mast cells of the peritoneal and pleura cavities were isolated from these animals. The cells were washed, resuspended in tris gel CM (the composition of tris gel CM buffer is as follows:

| | |
|---|---|
| tris | 25 mMol/l |
| NaCl | 120 mMol/l |
| CaCl$_2$ | 0.5 mMol/l |
| gelatin | 0.01% (% by weight) | the rest is water, the pH value of the solution is 7.6) buffer and pre-incubated with the test substances for 15 minutes at 37° C. The cells were then stimulated at 37° C. by adding the antigen EA to release histamine. After 30 minutes the cells were centrifuged off and the histamine released was determined in the cell supernatant using a fluorometric method (Shore et al. 1959, J. Pharmacol. Exp. Ther. 127, 182).

The compounds also displayed effects in inhibiting the anti-CD3-induced release of interleucin-4 and interleucin-5 according to the following instructions:

Inhibition of anti-CD3-induced release of interleucin (IL)-4 (CIL4TC) and IL-5-release (CIL5TC) in vitro The method described hereinbelow was carried out after Munoz et al. 1990, J. Immunol. 144, 964. Murine T-helper cells (D10.G4) were used as IL-4/IL-5-producing cells. These cells were pre-incubated with the test substances for 30 minutes at 37° C. The cells were then stimulated at 37° C. to produce interleucins by adding a monoclonal antibody against the T-cell receptor domain CD3 (anti-CD3). After 16 hours, the cells were centrifuged off and the released interleucins were quantified in the cell supernatant with ELISAs for murine IL-4 and IL-5.

Table of pharmacological experimental results

| Compound | CHIR [μmol/l] | CIL4TC [μmol/l] | CIL5TC [nmol/l] |
|---|---|---|---|
| D-22558 | IC50-0.016 | IC50-7967 | IC50-1521 |
| D-22559 | IC50-3.4 | 51% with 10 000 nmol/l | IC50-6601 |
| D-22561 | 15% with 10 | IC50-5683 | IC50-3214 |
| D-22685 | 33% with 10 | IC50-8577 | IC50-6887 |
| D-22686 | IC50-0.20 | 41% with 10 000 nmol/l | IC50-7314 |
| D-22693 | IC50-0.4 | 48% with 10 000 nmol/l | IC50-2702 |
| D-22697 | —,— | IC50-7287 | IC50-2881 |

-continued

Table of pharmacological experimental results

| Compound | CHIR [μmol/l] | CIL4TC [μmol/l] | CIL5TC [nmol/l] |
|---|---|---|---|
| D-22698 | —,— | 38% with 10 000 nmol/l | IC50-7765 |
| D-22992 | IC50-0.68 | IC50-9734 | IC50-6237 |
| D-22993 | IC50-0.54 | IC50-8973 | IC50-6935 |

CHIR = Inhibition of allergically-induced histamine release in vitro effect
Concentration unit: 10,000 nmol/l
Effect: % inhibition The in vitro investigations with D-22557 and D-22558 were continued in vivo (late phase eosinophilia model) in sensitised guinea pigs Method:

Male guinea pigs (Pirbright White, 200–250 g. Charles River Wiga, Sulfeld) were actively sensitised using a s.c. injection cf ovalbumin (10μg+100 mg aluminium hydroxide) and boosted 2 weeks later. One week after the booster injection the animals were exposed for 30 seconds to an aerosol made from 0.5% ovalbumin solution. 24 hours later brochoalveolar lavage (BAL) was carried out with 2×5 ml physiol. salt solution in animals sacrificed using an overdose of pentobarbital sodium and desanguinated. The lavage fluid was pooled, centrifuged for 10 minutes at 400×g and the cell pellet resuspended in 1 ml physiological salt solution. The eosinophiles were counted in a Neubauer chamber after staining by using a Becton Dickinson eosinophile test kit. Percentage Inhibition of the eosinophilia in the lavage was calculated in percent by comparing the eosinophile count of the groups treated with substance with the eosinolphile count of normal (unchallenged) and challenged control groups not treated with the substance. Each group numbered 10 animals. Test substances were either given prophylactically 2 hours before allergen challenge (−2 h) or therapeutically 4 hours after challenge (+4 h). When the therapeutic application was investigated, the animals (all groups) received azelastin (10 μg/kg po) 2 hours before allergen challenge to avoid deaths arising due to the onset of early phase bronchoconstriction.

Results:

| Substance | Dose (mg/kg) + Route | Time of treatment | % Inhibition |
|---|---|---|---|
| D-22557 | 0.5 ip | −2 h | 59% |
|  | 1 ip | −2 h | 42% |
|  | 5 ip | −2 h | 50% |
| D-22558 | 5 ip | −2 h | 41% |
| D-22558 | 10 po | −2 h | 23% |
|  | 30 po | −2 h | 35% |
| D-22558 | 10 ip | +4 h | 59% |

The processes for preparing the compounds of the invention are described by way of example in the following reaction diagrams I–VI and in general instructions. All the compounds can be prepared as described or by analogous means.

The compounds of general formula 1 with G=(i)

W=CH

X=CH

Y=single bond, such that the heterocyclic ring system is directly associated with the group

Z=O
may be obtained according to the following diagram:

DIAGRAM 1

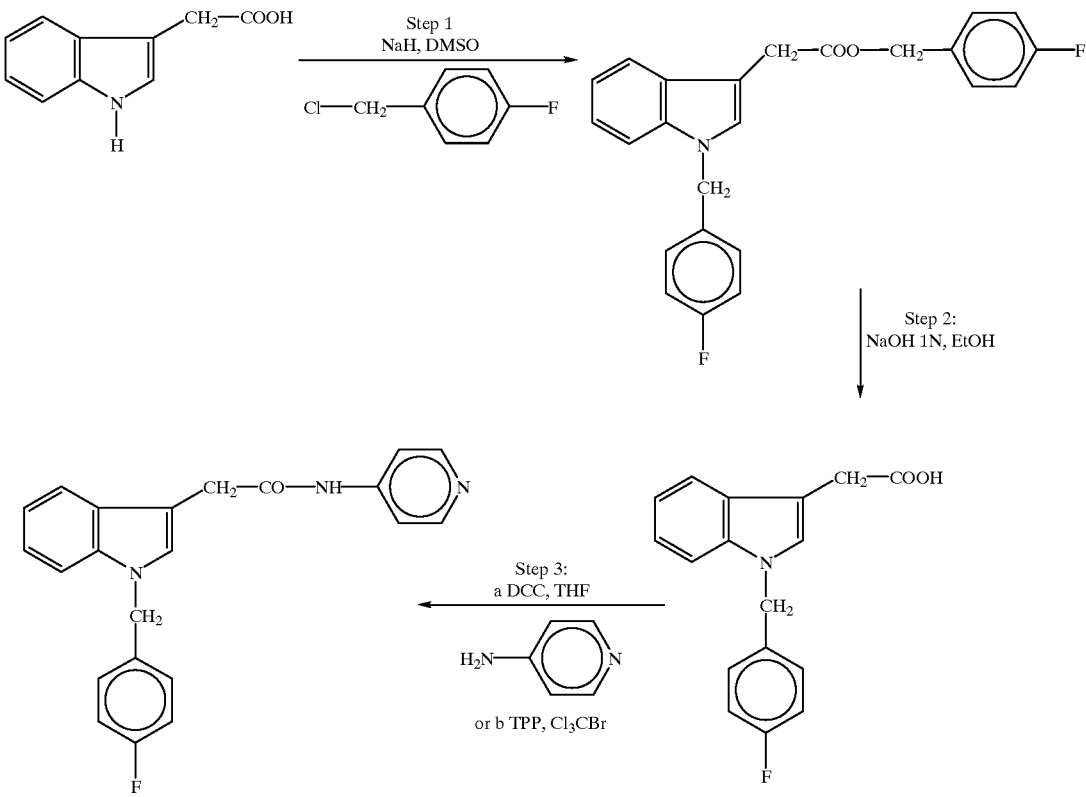

In accordance with the above diagram I, the 4-aminopyridine compound was obtained as well as the 3-aminopyridine compound.

N-(4-pyridyl)-[1-(4-fluorobenzyl)indole-3-yl]acetamide (D-22558)

Variant 1 for the Preparation of the Compound N-(4-Pyridyl)-[1-(4-fluorobenzyl)indole-3-yl]acetamide 1st step

[1-(4-fluorobenzyl)indole-3-yl]acetic acid-(4-fluorobenzyl)ester 100 ml dimethylsulfoxide (DMSO) are added to a three-necked flask under an $N_2$ atmosphere, 2.1 g sodium hydride (mineral oil suspension) are added with vigorous stirring and treated dropwise with a solution of 5 g (17.8 mmol) indole-3-acetic acid in 50 ml DMSO. 2.58 g (35.6 mMol) 4-fluorobenzyl chloride are added with further stirring. After 12 hours at 25° C. the reaction mixture is added to 300 ml water and extracted with ether. The organic phase is dried and the solvent is removed under reduced pressure. The residue is purified by column chromatography on silica gel.

Eluting mixture: methylene chloride/petroleum ether (80:20). Yield: 78% of theory.

2nd step

[1-(4-fluorobenzyl)indole-3-yl]acetic acid 8.7 g (22.2 mMol) [1-(4-fluorobenzyl)indole-3-yl]acetic acid (4-fluorobenzyl)ester are dissolved in 50 ml ethanol. 110 ml 1N sodium hydroxide solution are added and the mixture heated for 1 hour at reflux. After cooling, the aqueous phase is washed with ether, acidulated with concentrated hydrochloric acid and the precipitate filtered.

Yield: 6 g

3rd step

Preparation of the compound N-(4-pyridyl)-[1-(4-fluorobenzyl)indole-3-yl]acetamide (D-22558)

3.5 g (12.3 mMol) [1-(4-fluorobenzyl)indole-3-yl]acetic acid are dissolved in 100 ml anhydrous tetrahydrofuran. To this solution are added 2.54 g (12.3 mMol) dicyclohexyl-carbodiimide and 1.16 g (12.3 mMol) 4-aminopyridine. After stirring for 24 hours at 0° C., the formed dicyclohexyl urea is separated off. After mixing in the solvent, the residue is purified by column chromatography on silica gel. Eluting agent:

methylene chloride/ethanol: 95:5 (V/V). Yield: 65% of theory; Melting point: 55–60° C.

Elementary analysis:

| | | | |
|---|---|---|---|
| calc. | C 73.52 | H 5.05 | N 11.69 |
| found | C 73.18 | H 4.95 | N 11.45 |

General Instructions for the Preparation of the Compounds of General Formula 1 According to Diagram I 1st step:

The indole carboxylic acid derivative is added to a protic, dipolar aprotic or unpolar organic solvent such as isopropanol, THF, DMSO, DMA, dioxan, toluene, DMF, N-methylpyrrolidone or methylene chloride and added dropwise under $N_2$ atmosphere to a double molar suspension of a base prepared in a three-necked flask, such as sodium hydride, pulverised KOH, tert. BuOK, dimethylaminopyridine or sodium amide (mineral oil suspension) in a suitable solvent. The desired alkylaralkyl-, heteroaralkyl or aryl halide is added to the mixture, optionally in addition of a catalyst, such as Cu, and under stirring, for example in a range of 30 minutes to 3 hours, the temperature being maintained within a range from 0° C. to 120° C., preferably 30° C. to 80° C., particularly at 50° C.–60° C. When the reaction is completed, the reaction mixture is added to water, extracted for example with diethyl ether dichloromethane, methyl-tert.-butyl ether or tetrahydrofuran and the collected organic phase is dried with anhydrous sodium sulfate. The solvent is removed under reduced pressure, the residue crystallised by milling, or the oily residue is purified by recrystallisation, by column chromatography or by flash chromatography on silica gel or aluminium oxide. The eluting mixture is for example dichloromethane and diethylether in a ratio of 8:2 (Vol/Vol) or a mixture of dichloromethane and ethanol in a ratio of 9:1 (Vol/Vol).

2nd step:

The N-substituted indole carboxylic acid ester obtained according to the above instructions (1st step) is dissolved in ethanol and treated with 1N sodium hydroxide solution. The saponification reaction is carried out between 20° C. and 100° C., preferably between 40° C. and 80° C., particularly between 50° C. and 60° C. After 1–2 hours the mixture is cooled to room temperature, acidulated with hydrochloric acid or concentrated hydrochloric acid and the precipitated N-substituted indole acetic acid is isolated by filtration.

3rd step:

The acid obtained according to the above instructions (2nd step) is dissolved in anhydrous tetrahydrofuran. Dicyclohexyl carbodiimide is added as condensation agent followed by the substituted primary or secondary amine. After stirring for 24 hours at a temperature of 0° C.–50° C., preferably from 0° C.–30° C., particularly between 0° C. and –200° C., the formed urea is filtered. After evaporation of the solvent, the residue is recrystallised or purified chromatographically over silica gel. The eluting solvent used is, for example, a mixture of dichloromethane and ethanol (95:5 Vol/Vol).

Instead of dicyclohexylcarbodiimide (DCC) as condensation agent in the condensation reaction in step 3 it is also possible to use diisopropylcarbodiimide (DIC) as condensation agent.

The condensation reaction of step 3 can, however, also be carried out using triphenylphosphine and bromotrichloromethane in THF at a temperature of 30° C.–70° C. instead of using DCC/THF or DIC/THF. Furthermore, the combinations carbonyldiimidazole in anhydrous THF were used for the condensation reaction (step 3) at a temperature of 0° C. to 60° C., preferably at 10° C.–30° C., particularly at 25° C. As an additional condensation agent used in the condensation reaction in step 3, the combination 1-methyl-2-chloropyridinium iodide with triethylamine was used in dichloromethane at a temperature of 0° C.–80° C., preferably between 30° C. and 70° C., particularly between 50° C. and 60° C.

According to these general instructions for steps 1–3, the following compounds were synthesised and are listed in the following summary, quoting their code numbers (D-number) and the corresponding chemical designation. The following table 1 shows, the structures of these compounds, their melting points and $R_F$ values as well as the coupling reagents used for their preparation in the condensation reaction (step 3) from the general formula 1 and the substituents Y-G, X, $R^1$, $R^2$, $R^3$ and W:

A: dicyclohexylcarbodiimide or diisopropylcarbodiimide solvent:anhydrous tetrahydrofuran (DCC(DIC)/THF)

B: triphenylphosphine/bromotrichloromethane ($Ph_3P$/$BrCCl_3$/THF)

C: carbonyldiimidazole/TMF(CDI)THF)

D: 1-methyl-2-chloropyridinium iodide/triethylamine in the solvent methylene chloride

| | |
|---|---|
| D-22553 | N-(3-pyridyl-yl)-(1-methylindole-3-yl)acetamide |
| D-22560 | N-(4-pyridyl-yl)-(1-benzylindole-3-yl)acetamide |
| D-22680 | N-(3-pyridyl-yl)-(1-benzylindole-3-yl)acetamide |
| D-22681 | N-(3-pyridyl-yl)-1-[(4-fluorobenzylindole-3-yl]propionamide |
| D-22684 | N-(3-pyridyl-yl)-3-(1-methylindole-3-yl)propionamide |
| D-23198 | 1-(3-(1-(4-fluorobenzyl)indole-3-yl)propionamide)-4-(4-chlorophenyl)piperazine |
| D-23245 | N-(4-pyridyl-yl)-4-(1-(4-fluorobenzyl)indole-3-yl)butyramide |
| D-23496 | N-(2,6-dimethylpyridine-2-yl)-2-[1-(4-fluorobenzyl)indole-3-yl]acetamide |
| D-22682 | N-(3-pyridyl-yl)-3-(1-benzylindole-3-yl)propionamide |
| D-22683 | N-(4-pyridyl-yl)-3-(1-benzylindole-3-yl)propionamide |
| D-22689 | N-(4-pyridyl-yl)-3-(1-methylindole-3-yl)propionamide |
| D-22690 | N-(4-pyridyl-yl)-3-[1-(4-fluorobenzyl)indole-3-yl]propionamide |
| D-22691 | N-(4,6-dimethylpyridine-2-yl)-3-[1-(4-fluorobenzyl)indole-3-yl]propionamide |
| D-22693 | N-(4-pyridyl-yl)-2-(1-ethylindole-3-yl)acetamide |
| D-22694 | N-(4,6-dimethylpyridine-2-yl)-2-(1-ethylindole-3-yl)acetamide |
| D-22695 | N-(4,6-dimethylpyridine-2-yl)-2-(1-benzylindole-3-yl)acetamide |
| D-23489 | N-(3-pyridyl)-4-(1-benzylindole-3-yl)butyramide |
| D-23490 | N-(4-pyridyl)-4-(1-benzylindole-3-yl)butyramide |
| D-23495 | N-(3-pyridyl)-2-[1-(4-fluorobenzyl)indole-3-yl]acetamide |
| D-23705 | N-(2-pyridyl)-3-(1-benzylindole-3-yl)propionamide |
| D-23725 | N-(2-pyridyl)-2-(1-benzylindole-3-yl)acetamide |
| D-23728 | N-(2-pyridyl)-3-[1-(4-fluorobenzyl)indole-3-yl]propionamide |
| D-22552 | N-(4-pyridyl)-4-(indole-3-yl)butyramide |
| D-22701 | N-(4,6-dimethylpyridine-2-yl)-3-(benzylindole-3-yl)propenamide |
| D-23200 | (N-(4,6-dimethylpyridine-2-yl)-3-[1-(4-fluorobenzyl)indole-3-yl]propionamide |
| D-22940 | 1-[2-(indole-3-yl)acetamide]-4-(4-chlorophenyl)piperazine |
| D-22941 | 1-[2-(indole-3-yl)acetamide]-4-(4,4'-bisfluorobenzhydryl)piperazine |
| D-22943 | 1-[2-(indole-3-yl)acetamide]-4-methylpiperazine |
| D-23197 | 1-[3-(indole-3-yl)propionamide]-4-(4,4'-bisfluorobenzhydryl)piperazine |
| D-23247 | N-(4-pyridyl)-3-(1-benzyl-5-methoxyindole-3-yl)propionamide |
| D-23246 | N-(4-pyridyl)-3-[1-(4-fluorobenzyl)-5-fluoroindole-3-yl]propionamide |
| D-23244 | N-(4-pyridyl)-3-(1-benzyl-5-fluoroindole-3-yl)propionamide |
| D-22946 | 1-[3-(indole-3-yl)propionamide]-4-(4-chlorophenyl)-piperazine |
| D-22945 | 1-[3-(indole-3-yl)propionamide]-4-(4-methoxyphenyl)piperazine |
| D-22944 | 1-[3-(indole-3-yl)propionamide]-4-methylpiperazine |
| D-22942 | 1-[2-(indole-3-yl)acetamide]-4-(4-methoxyphenyl)piperazine |
| D-23243 | N-(4-pyridyl)-3-(1-benzylindole-3-yl)acrylamide |
| D-23242 | N-(4-pyridyl)-3-(5-chloroindole-3-yl)propionamide |

-continued

| | |
|---|---|
| D-23241 | N-(4-pyridyl)-3-(5-chloroindole-3-yl)propionamide |
| D-23240 | N-(4-pyridyl)-3-(5-methoxyindole-3-yl)propionamide |
| D-23239 | N-(4-pyridyl)-3-[1-(4-fluorobenzyl)-5-isopropyl-indole-3-yl]propionamide |
| D-23238 | N-(4-pyridyl)-3-(5-isopropylindole-3-yl)propionamide |
| D-23488 | N-(4-pyridyl)-2-(5-chloroindole-3-yl)acetamide |
| D-23491 | N-(4-pyridyl)-2-[1-(4-fluorobenzyl)-2-methyl-5-isopropylindole-3-yl]acetamide |
| D-23492 | N-(4-pyridyl)-2-(1-benzyl-5-fluoroindole-3-yl)acetamide |
| D-23493 | N-(4-pyridyl)-2-[1-(4-fluorobenzyl)-5-chloroindole-3-yl]acetamide |
| D-23494 | N-(4-pyridyl)-2-[1-(4-fluorobenzyl)-5-fluoroindole-3-yl]acetamide |
| D-23497 | N-(4-pyridyl)-2-(2-methyl-5-isopropylindole-3-yl)acetamide |
| D-23498 | N-(4-pyridyl)-3-[1-(4-fluorobenzyl)-5-methoxyindole-3-yl]propionamide |
| D-23499 | N-(4-pyridyl)-2-(2-methyl-5-chloroindole-3-yl)-acetamide |
| D-23500 | N-(4-pyridyl)-3-(1-benzyl-5-isopropylindole-3-yl)propionamide |
| D-23501 | N-(4-pyridyl)-2-(1-benzyl-2-methyl-5-fluoro-indole-3-yl)acetamide |
| D-23502 | N-(4-pyridyl)-2-(2-methyl-5-methoxyindole-3-yl)-acetamide |
| D-23703 | N-(4-pyridyl)-2-(5-methoxy-1H-indole-3-yl)-acetamide |
| D-23721 | N-(4-pyridyl)-3-[5-chloro-1-(4-fluorobenzyl)-indole-3-yl]propionamide |
| D-23735 | N-(4-pyridyl)-2-(1-benzyl-5-chloroindole-3-yl)acetamide |
| D-23727 | N-(4-pyridyl)-2-[1-(4-fluorobenzyl)-5-isopropyl-indole-3-yl]acetamide |
| D-23707 | N-(4-pyridyl)-2-(5-fluoro-2-methylindole-3-yl)acetamide |
| D-223712 | N-(4-pyridyl)-2-[1-(4-fluorobenzyl)-2-methyl-5-fluoroindole-3-yl]acetamide |
| D-23708 | N-(4-pyridyl)-2-(1-benzyl-2-methyl-5-isopropylindole-3-yl)acetamide |
| D-23729 | N-(4-pyridyl)-3-(1-benzyl-5-chloroindole-3-yl)propionamide |
| D-23702 | N-(4-pyridyl-yl)-2-[1-(4-fluorobenzyl)-2-methyl-5-methoxyindole-3-yl]acetamide |
| D-23718 | N-(4-pyridyl-yl)-2-[1-(4-fluorobenzyl)-2-methyl-5-chloroindole-3-yl]acetamide |
| D-23722 | N-(4-pyridyl-yl)-3-[1-(4-fluorobenzyl)indole-3-yl]acrylamide |
| D-23724 | N-(4-pyridyl-yl)-2-(1-benzyl-5-isopropylindole-3-yl]acetamide |
| D-23701 | N-(2-pyridyl-yl)-2-[1-(4-fluorobenzyl)indole-3-yl]acetamide |
| D-23711 | N-(4-pyridyl-yl)-2-(5-isopropyl-1H-indole-3-yl]acetamide |
| D-23726 | N-(4-pyridyl-yl)-2-(5-fluoro-1H-indole-3-yl]acetamide |
| D-23698 | N-(4-pyridyl-yl)-2-[1-benzyl-5-methoxyindole-3-yl]acetamide |
| D-23700 | (E)-N-(4,6-dimethylpyridine-2-yl)-3-(1-methyl-indole-3-yl)acrylamide |
| D-23719 | N-(4-pyridyl-yl)-2-[1-(4-fluorobenzyl)-5-fluoro(indole-3-yl)]acetamide |
| D-23732 | N-[2,6-dimethyl-(4-pyrimidyl]-2-[1-(4-fluorophenyl)-5-fluoro(indole-3-yl)acetamide |
| D-23717 | N-(4-pyridyl-yl)-2-[1-(4-fluorophenyl)-indole-3-yl]acetamide |
| D-23733 | N-[2,6-dimethyl-(4-pyrimidyl]-2-[1-(4-fluorophenyl)-indole-3-yl]acetamide |
| D-23734 | N-(4-pyridyl-yl)-2-[1-(4-fluorophenyl)-5-methoxy-indole-3-yl]acetamide |
| D-23730 | N-(4-pyridyl)-3-[(5-benzyloxy-1H-(indole-3-yl]propionamide |
| D-23720 | N-(4-pyridyl-yl)-2-[1-(4-fluorophenyl)-6-methoxy-indole-3-yl]acetamide |
| D-24034 | N-(4-pyridyl)-2-[(1-n-butyl-(indole-3-yl))acetamide |
| D-24035 | N-(4-pyridyl)-2-[1-(4-chlorobenzyl)-(indole-3-yl)]acetamide |
| D-24036 | N-(4-pyridyl)-2-[1-(3-fluorobenzyl)-indole-3-yl]acetamide |
| D-24040 | N-(4-pyridyl)-2-[1-(2-fluorobenzyl)-indole-3-yl)acetamide |
| D-24041 | N-(4-pyridyl)-2-[1-(3-trifluoromethylbenzyl)-indole-3-yl]acetamide |
| D-24042 | N-(2-pyridyl)-ethyl-2-[1-(4-fluoro-benzyl)indole-3-yl]acetamide |
| D-24236 | N-[(2-pyridyl)-methyl]-{1-(4-fluorobenzyl)-indole-3-yl]acetamide |
| D-24244 | N-[4-(4-pyridyl)-methyl)phenyl]-2-[1-(4-fluorobenzyl)indole-3-yl]acetamide |
| D-24238 | N-[(3-pyridyl)-methyl]-[1-(4-fluoro-benzyl)indole-3-yl]acetamide |
| D-24239 | N-[(4-pyridyl)-methyl]-[1-(4-fluoro-benzyl)indole-3-yl]acetamide |
| D-23714 | N-(4-pyridyl)-2-[1-(4-fluorobenzyl)-6-hydroxyindole-3-yl]acetamide |

TABLE 1
New indole derivatives according to reaction diagram 1
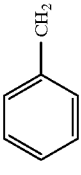
| D | Y—G | | X | R¹ | R² | R³ | W | Fp[°C.] | CR |
|---|---|---|---|---|---|---|---|---|---|
| 22553 | CH₂—CO—NH— | 3-pyridyl | CH | CH₃ | H | H | CH | 152 | A |
| 22560 | CH₂—CO—NH— | 4-pyridyl | CH |  | H | H | CH | 40–60 (deliquesce) | A |
| 22680 | CH₂—CO—NH— | 3-pyridyl | CH |  | H | H | CH | 160 | A |
| 22681 | CH₂CH₂—CO—NH— | 3-pyridyl | CH |  (4-F-benzyl) | H | H | CH | 116 | A |
| 22684 | CH₂CH₂—CO—NH— | 3-pyridyl | CH | CH₃ | H | H | CH | 129 | A |
| 23198 | (CH₂)₂—CO—N(piperazinyl)-4-Cl-phenyl | | CH |  (4-F-benzyl) | H | H | CH | oil | D |

TABLE 1-continued
New indole derivatives according to reaction diagram 1
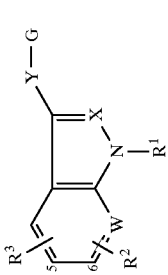
| D | | R¹ | R² | R³ | W | Fp[° C.] | CR |
|---|---|---|---|---|---|---|---|
| 23245 | (CH₂)₃—CO—NH—[4-pyridyl] | 4-F-C₆H₄-CH₂ | H | H | CH | oil | D |
| 23496 | CH₂—CO—NH—[4,6-dimethyl-pyridin-2-yl] | 4-F-C₆H₄-CH₂ | H | H | CH | 132 | D |
| 22682 | (CH₂)₂—CO—NH—[3-pyridyl] | C₆H₅-CH₂ | H | H | CH | 120 | A |
| 22683 | (CH₂)₂—CO—NH—[4-pyridyl] | 4-F-C₆H₄-CH₂ | H | H | CH | 154 | A |
| 22689 | (CH₂)₂—CO—NH—[4-pyridyl] | CH₃ | H | H | CH | 118 | A |
| 22690 | (CH₂)₂—CO—NH—[4-pyridyl] | 4-F-C₆H₄-CH₂ | H | H | CH | 125 | A |

TABLE 1-continued

New indole derivatives according to reaction diagram 1

| D | G | X | R¹ | R² | R³ | W | Fp[° C.] | CR |
|---|---|---|----|----|----|---|----------|-----|
| 22691 | (CH₂)₂—CO—NH-(2-pyridyl) | CH | | H | H | CH | 40–60 (deliquesce) | B |
| 22693 | CH₂—CO—NH-(4-pyridyl) | CH | CH₂CH₃ | H | H | CH | 130–132 | A |
| 22694 | CH₂—CO—NH-(4,6-dimethyl-2-pyridyl) | CH | CH₂CH₃ | H | H | CH | 159 | B |
| 22695 | CH₂—CO—NH-(4,6-dimethyl-2-pyridyl) | CH | CH₂-phenyl | H | H | CH | 40–60 (deliquesce) | B |
| 23489 | (CH₂)₃—CO—NH-(3-pyridyl) | CH | CH₂-phenyl | H | H | CH | 110 | D |

TABLE 1-continued
New indole derivatives according to reaction diagram 1
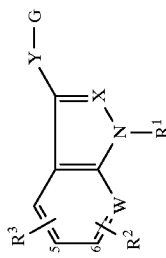
| D | | X | $R^1$ | $R^2$ | $R^3$ | W | Fp[° C.] | CR |
|---|---|---|---|---|---|---|---|---|
| 23490 | (CH$_2$)$_3$—CO—NH—[4-pyridyl] | CH | —CH$_2$—C$_6$H$_5$ | H | H | CH | 93 | D |
| 23495 | CH$_2$—CO—NH—[3-pyridyl] | CH | —CH$_2$—C$_6$H$_4$—F | H | H | CH | 145 | D |
| 23705 | (CH$_2$)$_2$—CO—NH—[2-pyridyl] | CH | —CH$_2$—C$_6$H$_5$ | H | H | CH | 116–118 | D |
| 23725 | CH$_2$—CO—NH—[3-pyridyl] | CH | —CH$_2$—C$_6$H$_5$ | H | H | CH | 118–120 | D |
| 23728 | (CH$_2$)$_2$—CO—NH—[2-pyridyl] | CH | —CH$_2$—C$_6$H$_4$—F | H | H | CH | 104–105 | D |
| 22552 | (CH$_2$)$_3$—CO—NH—[4-pyridyl] | CH | H | H | H | CH | 91 | A |

TABLE 1-continued

New indole derivatives according to reaction diagram 1

| D | R Y—G | X | R¹ | R² | R³ | W | Fp[° C.] | CR |
|---|---|---|---|---|---|---|---|---|
| 22701 | 2,4-dimethyl-6-(CH=CH—CO—NH)-pyridine; CH₂—phenyl | CH | H | H | H | CH | 174 | B |
| 23200 | 2,4-dimethyl-6-(CH=CH—CO—NH)-pyridine; CH₂—(4-F-phenyl) | CH | H | H | H | CH | oil | B |
| 22940 | 4-(4-Cl-phenyl)-piperazin-1-yl-CO—CH₂ | CH | H | H | H | CH | 236–238 | C |
| 22941 | 4-[CH(4-F-phenyl)₂]-piperazin-1-yl-CO—CH₂ | CH | H | H | H | CH | 162–164 | C |

TABLE 1-continued
New indole derivatives according to reaction diagram 1
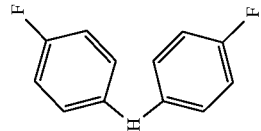
| D | R¹ | X | R² | R³ | W | Fp[° C.] | CR |
|---|---|---|---|---|---|---|---|
| 22943 | 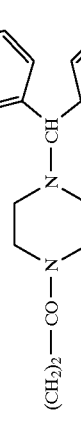 | CH | H | H | CH | 152–154 | C |
| 23197 |  | CH | H | H | CH | 190–192 | D |
Y—G
| D | Y—G | X | R² | R³ | W | Fp[° C.] | CR |
|---|---|---|---|---|---|---|---|
| 23247 | (CH₂)₂—CO—NH— | CH | CH₂ | 5-OCH₃ | H | CH | 60–70 (deliquesce) | D |
| 23246 | (CH₂)₂—CO—NH— | CH | CH₂ (4-F) | 5-F | H | CH | 60–70 (deliquesce) | D |
| 23244 | (CH₂)₂—CO—NH— | CH | CH₂ | 5-F | H | CH | 185 | D |

TABLE 1-continued
New indole derivatives according to reaction diagram 1
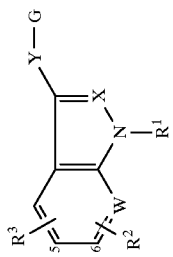
| D | | X | R¹ | R² | R³ | W | Fp[° C.] | CR |
|---|---|---|---|---|---|---|---|---|
| 22946 | (CH₂)₂—CO—N(piperazine)N—C₆H₄—Cl(4) | CH | H | H | H | CH | 189–191 | C |
| 22945 | (CH₂)₂—CO—N(piperazine)N—C₆H₄—OCH₃(4) | CH | H | H | H | CH | 170–172 | C |
| 22944 | (CH₂)₂—CO—N(piperazine)N—CH₃ | CH | H | H | H | CH | 154–156 | C |
| 22942 | CH₂—CO—N(piperazine)N—C₆H₄—OCH₃(4) | CH | H | H | H | CH | 174–176 | C |
| 23243 | HC=CH—CO—NH—(4-pyridyl) | CH | CH₂—C₆H₅ | H | H | CH | 239–240 | D |
| 23242 | (CH₂)₂—CO—NH—(4-pyridyl) | CH | H | 5-Cl | H | CH | 189 | D |
| 23241 | (CH₂)₂—CO—NH—(4-pyridyl) | CH | H | 5-F | H | CH | 150–160 | D |

TABLE 1-continued

New indole derivatives according to reaction diagram 1

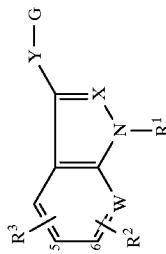

| D | | R¹ | R² | R³ | W | Fp[° C.] | CR |
|---|---|---|---|---|---|---|---|
| 23240 | (CH₂)₂—CO—NH—[4-pyridyl] | H | 5-OCH₃ | H | CH | 142 | D |
| 23239 | (CH₂)₂—CO—NH—[4-pyridyl] | 4-F-benzyl (CH₂-C₆H₄-F) | 5-CH(CH₃)₂ | H | CH | 45–55 (deliquesce) | D |
| 23238 | (CH₂)₂—CO—NH—[4-pyridyl] | H | 5-CH(CH₃)₂ | H | CH | 70–78 (deliquesce) | D |
| 23488 | CH₂—CO—NH—[4-pyridyl] | H | 5-Cl | H | CH | 200 (disint.) | D |
| 23491 | CH₂—CO—NH—[4-pyridyl] | 4-F-benzyl (CH₂-C₆H₄-F) | 5-CH(CH₃)₂ | H | CH | 174 | D |
| 23493 | CH₂—CO—NH—[4-pyridyl] | 4-F-benzyl (CH₂-C₆H₄-F) | 5-Cl | H | CH | 150–156 | D |

Note: X = CH for rows 23240, 23239, 23238, 23488; X = CH₃ for rows 23491, 23493.

TABLE 1-continued

New indole derivatives according to reaction diagram 1

| D | | R1 | X | R2 | R3 | W | Fp[° C.] | CR |
|---|---|---|---|---|---|---|---|---|
| 23494 | CH₂—CO—NH—(4-pyridyl) | 4-F-C₆H₄-CH₂ | CH | 5-F | H | CH | 70–76 (deliquesce) | D |
| 23497 | CH₂—CO—NH—(4-pyridyl) | H | C—CH₃ | 5-CH(CH₃)₂ | H | CH | 209 | D |
| 23492 | CH₂—CO—NH—(4-pyridyl) | C₆H₅-CH₂ | CH | 5-F | H | CH | 130–137 | D |
| 23498 | (CH₂)₂—CO—NH—(4-pyridyl) | C₆H₅-CH₂ | CH | 5-OCH₃ | H | CH | 144 | D |
| 23499 | CH₂—CO—NH—(4-pyridyl) | H | C—CH₃ | 5-Cl | H | CH | >250 | D |
| 23500 | (CH₂)₂—CO—NH—(4-pyridyl) | C₆H₅-CH₂ | CH | 5-CH(CH₃)₂ | H | CH | 50 (deliquesce) | D |

TABLE 1-continued
New indole derivatives according to reaction diagram 1
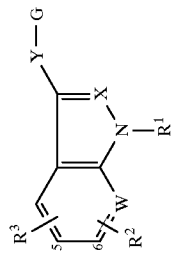
| D | | R1 | X | R2 | R3 | W | Fp[° C.] | CR |
|---|---|---|---|---|---|---|---|---|
| 23501 | 4-Pyridyl-NH-CO-CH2- | CH2-C6H5 | C—CH3 | 5-F | H | CH | 85-90 | D |
| 23502 | 4-Pyridyl-NH-CO-CH2- | H | C—CH3 | 5-OCH3 | H | CH | 203 | D |
| 23703 | 4-Pyridyl-NH-CO-CH2- | H | CH | 5-OCH3 | H | CH | 166-167 | D |
| 23721 | 4-Pyridyl-NH-CO-(CH2)2- | CH2-C6H4-4-F | CH | 5-Cl | H | CH | 58-60 (deliquesce) | D |
| 23735 | 4-Pyridyl-NH-CO-CH2- | CH2-C6H5 | CH | 5-Cl | H | CH | 138-140 | D |
| 23727 | 4-Pyridyl-NH-CO-CH2- | CH2-C6H4-4-F | CH | 5-CH(CH3)2 | H | CH | 88 | D |
| 23707 | 4-Pyridyl-NH-CO-CH2- | H | C—CH3 | 5-F | H | CH | 200 (disinte.) | D |

TABLE 1-continued

New indole derivatives according to reaction diagram 1

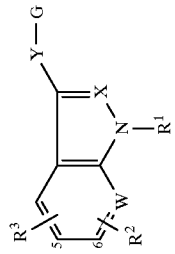

| D | | X | R¹ | R² | R³ | W | Fp[° C.] | CR |
|---|---|---|---|---|---|---|---|---|
| 23712 | CH₂—CO—NH-(4-pyridyl) | C—CH₃ | 4-F-benzyl (CH₂-C₆H₄-F) | 5-F | H | CH | 95-105 (deliquesce) | D |
| 23708 | CH₂—CO—NH-(4-pyridyl) | C—CH₃ | benzyl (CH₂-C₆H₅) | 5-CH(CH₃)₂ | H | CH | 164 | D |
| 23729 | (CH₂)₂—CO—NH-(4-pyridyl) | CH | benzyl (CH₂-C₆H₅) | 5-Cl | H | CH | 160 | D |
| 23702 | CH₂—CO—NH-(4-pyridyl) | C—CH₃ | 4-F-benzyl (CH₂-C₆H₄-F) | 5-OCH₃ | H | CH | 162 | D |
| 23718 | CH₂—CO—NH-(4-pyridyl) | C—CH₃ | 4-F-benzyl (CH₂-C₆H₄-F) | 5-Cl | H | CH | 145 | D |
| 23722 | CH=CH—CONH-(4-pyridyl) | CH | 4-F-benzyl (CH₂-C₆H₄-F) | H | H | CH | >250 | D |

TABLE 1-continued
New indole derivatives according to reaction diagram 1
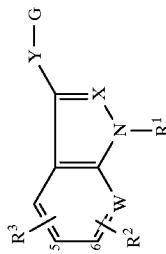
| D | G | R1 | X | R2 | R3 | W | Fp[° C.] | CR |
|---|---|---|---|---|---|---|---|---|
| 23724 | 4-pyridyl-NH-CO-CH2- | CH2-C6H5 | CH | 5-CH(CH3)2 | H | CH | 67-68 | D |
| 23701 | 2-pyridyl-NH-CO-CH2- | 4-F-C6H4-CH2- | CH | H | H | CH | 110-111 | D |
| 23711 | 4-pyridyl-NH-CO-CH2- | H | CH | CH(CH3)2 | H | CH | 174 | D |
| 23726 | 4-pyridyl-NH-CO-CH2- | H | CH | 5-F | H | CH | 200 (disinte.) | D |
| 23698 | 4-pyridyl-NH-CO-CH2- | CH2-C6H5 | CH | 5-OCH3 | H | CH | 145-146 | D |
| 23700 | (4,6-dimethyl-2-pyridyl)-NH-CO-CH=CH- | CH3 | CH | H | H | CH | 162-163 | D |

TABLE 1-continued
New indole derivatives according to reaction diagram 1
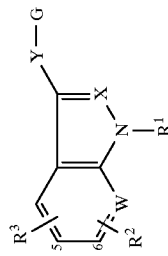
| D | | X | R¹ | R² | R³ | W | Fp[° C.] | CR |
|---|---|---|---|---|---|---|---|---|
| 23719 | CH₂—CO—NH-(4-pyridyl) | CH | 4-F-phenyl | 5-F | H | CH | 186 | D |
| 23732 | CH₂—CO—NH-(2,6-dimethylpyrimidin-4-yl) | CH | 4-F-phenyl | 5-F | H | CH | 55 (deliquesce) | D |
| 23717 | CH₂—CO—NH-(4-pyridyl) | CH | 4-F-phenyl | H | H | CH | 152 | D |
| 23733 | CH₂—CO—NH-(2,6-dimethylpyrimidin-4-yl) | CH | 4-F-phenyl | H | H | CH | 55 (deliquesce) | D |
| 23734 | CH₂—CO—NH-(4-pyridyl) | CH | 4-F-phenyl | 5-OCH₃ | H | CH | 218 | D |

TABLE 1-continued
New indole derivatives according to reaction diagram 1
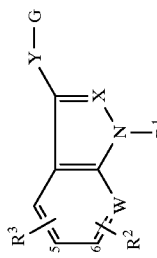
| D | | X | R¹ | | R² | R³ | W | Fp[° C.] | CR |
|---|---|---|---|---|---|---|---|---|---|
| 23730 | (CH₂)₂—CO—NH—[4-pyridyl] | CH | H | | 5—OCH₂—[phenyl] | H | CH | 170 | D |
| 23720 | CH₂—CO—NH—[4-pyridyl] | CH | [4-F-phenyl] | | 6-OCH₃ | H | CH | 152 | D |
| 24034 | CH₂—CO—NH—[4-pyridyl] | CH | CH₂CH₂CH₂CH₃ | | H | H | CH | oil | D |
| 24035 | CH₂—CO—NH—[4-pyridyl] | CH | CH₂—[4-Cl-phenyl] | | H | H | CH | 153 | D |
| 24036 | CH₂—CO—NH—[4-pyridyl] | CH | CH₂—[3-F-phenyl] | | H | H | CH | 161 | D |
| 24040 | CH₂—CO—NH—[4-pyridyl] | CH | CH₂—[2-F-phenyl] | | H | H | CH | 146 | D |

TABLE 1-continued
New indole derivatives according to reaction diagram 1
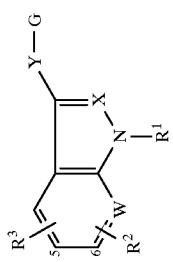
| D | | X | R¹ | R² | R³ | W | Fp[° C.] | CR |
|---|---|---|---|---|---|---|---|---|
| 24041 | CH₂—CO—NH—(4-pyridyl) | CH | 3-CF₃-phenyl-CH₂ | H | H | CH | 127 | D |
| 24042 | CH₂—CONH—(CH₂)₂—(2-pyridyl) | CH | 4-F-phenyl-CH₂ | H | H | CH | 87 | D |
| 24236 | CH₂—CONH—CH₂—(2-pyridyl) | CH | 4-F-phenyl-CH₂ | H | H | CH | 75 | D |
| 24244 | CH₂—CO—NH—(4-(4-pyridyl-CH₂)-phenyl) | CH | 4-F-phenyl-CH₂ | H | H | CH | 118 | D |
| 24238 | CH₂—CONH—CH₂—(3-pyridyl) | CH | 4-F-phenyl-CH₂ | H | H | CH | 163 | D |
| 24239 | CH₂—CONH—CH₂—(4-pyridyl) | CH | 4-F-phenyl-CH₂ | H | H | CH | 139–140 | D |

TABLE 1-continued

New indole derivatives according to reaction diagram 1

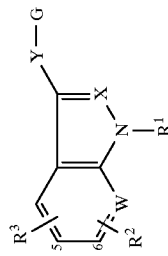

| D | | X | R¹ | R² | R³ | W | Fp[° C.] | CR |
|---|---|---|---|---|---|---|---|---|
| 23714 | CH₂—CO—NH-(4-pyridyl) | CH | 4-F-benzyl (CH₂-C₆H₄-F) | 6-OH | H | CH | 213 | — |
| 23635 | CH₂—CO—NH-(4-pyridyl) | CH | 2-quinolinylmethyl | H | H | CH | 79 (disint.) | D |
| 23644 | CH₂—CO—NH-(2-pyridyl) | CH | 2-quinolinylmethyl | H | H | CH | 54 (disint.) | D |
| 23681 | CH₂—CO—NH-(3-quinolinyl) | CH | 2-quinolinylmethyl | H | H | CH | 156–161 | D |
| 23767 | CH₂—CO—NH-(3-pyridyl) | CH | 2-quinolinylmethyl | H | H | CH | 118–120 | D |
| 23784 | CH₂—CO—NH-(3-pyridyl) | CH | 2-pyridinylmethyl | H | H | CH | 144–145 | D |

TABLE 1-continued

New indole derivatives according to reaction diagram 1

| D | | X | R$^1$ | R$^2$ | R$^3$ | W | Fp[°C.] | CR |
|---|---|---|---|---|---|---|---|---|
| 23785 | CH$_2$—CO—NH-(2-pyridyl) | CH | CH$_2$-(2-pyridyl) | H | H | CH | 111–112 | D |
| 23841 | CH$_2$—CO—NH-(4-pyridyl) | CH | CH$_2$-(2-pyridyl) | H | H | CH | 181–183 (oxalate) | D |

Starting compounds for the compounds of general formula 1, prepared according to synthesis diagram I, which emerge from table 1 (intermediate syntheses):
Final synthesis steps
(D-compounds) of general formula 1 from table I and their primary steps
A) 22558, 22560, 22680, 22693, 22694, 22695, 22940, 22941, 22943, 22942, 22944, 22945, 23495, 23496, 23699 23701, 23725, 23635, 23644, 23681, 22553, 23767
(N-alkylation agent: $CH_3$) instead of 4-fluorobenzylchloride in diagram 1)
from (indole-3-yl)acetic acid (commercially available);
B) 24035, 24040, 24041, 24042, 24236, 24244, 24238, 24239, 23784, 23785, 23841
from (indole-3-yl)acetic acid ethyl ester (commercially available);
C) 22681, 22682, 22683, 22684, 22689, 22690, 22691, 22946, 23197, 23198, 23728, 23705,
from (indole-3-yl)acetic acid ethyl ester (commercially available);
D) 22552, 23245, 23489, 23490
from (indole-3-yl)butyric acid (commercially available);
E) 23492, 23494, 23726
from (5-fluoro-indole-3-yl)acetic acid (commercially available);
Continuation of the intermediate syntheses for the compounds of the general formula of table 1
F) 23703, 23698
from (5-methoxyindole-3-yl)acetic acid (commercially available);
G) 23238, 23239, 23240, 23241, 23242, 23244, 23246, 23247, 23498, 23500, 23730
The C-5-substituted (indole-3-yl)propionic acids are synthesised by analogy with the following literature reference:
L. Kalb, F. Schweizer, Chem. Ber. 59, 1860 (1926)
H) 23488, 23491, 23493, 23497, 23499, 23501, 23502, 23721, 23735, 23427, 23707, 23712, 23708, 23729, 23702, 23718, 23724, 23727, 23711, 23720
The C-2-, C-5- and C-6-substituted indole-3-yl acetic acid derivatives that were needed as primary steps were synthesised according to the following literature instructions:
a) S. Findlay and G. Dougherty,
J. Org. Chem. 13, 560 (1948)
b) H. Yao and P. Resnick, J. Amer. Chem. 84, 3514 (1962)
c) H. Plieninger, Chem.Ber. 87. 228 (1954)
d) Houben-Weyl E6bl "Hetarene I—Part 2a", p. 716–720, Georg Thieme Publishers, Stuttgart—New York (1994)
Continuation of the intermediate syntheses for the compounds of table 1
I) 23243, 23722, 22701
(N-benzyl-3-yl)acrylic acid or N-[4-(fluorobenzyl) indole-3-yl]acrylic acid were prepared according to the synthesis path described hereinbelow and the corresponding synthesis instructions:
Synthesis instructions:
1-benzyl-(indole-3-yl)carboxaldehyde
To a solution of 10 g (68.9 mMol) indole-3-carboxaldehyde in 50 ml dioxan are added 13.5 g $K_2CO_3$ and 9 ml (75 mMol) benzylbromide. After stirring 12 hours at room temperature 200 ml water are added and the mixture is extracted with methylene chloride. The organic phase is washed with water, dried with sodium sulfate and concentrated in vacuum. After purification by column chromatography (eluting solvent: dichloromethane), 14.2 g of the desired compound are obtained. Yield: 88% of theory
(1-benzylindole-3-yl)acrylic acid methylester
8 g (34 mMol) 1-benzyl(indole-3-yl)carboxaldehyde and 25 g (74.8 mMol) triphenylphosphoranylide acetic acid methyl ester in 200 ml dioxan are refluxed for 48 hours. The dioxan is evaporated and under reduced pressure the residue is purified by column chromatography in silica gel with a mixture of dichloromethane/hexane 80:20. 8.9 g of yellow crystals are obtained.
Yield: 90% of theory. (
1-benzylindole-3-yl)acrylic acid
43 ml (87 mMol) sodium hydroxide solution are added to a solution of 8.5 g (29,2 mMol) of the above ester in 50 ml ethanol. The mixture is refluxed for 1 hour. After cooling, 200 ml water are added, and the mixture is acidulated with conc. HCl. The (1-benzylindole-3-yl)acrylic acid precipitates in the form of white crystals. Yield: 88% of theory
Continuation of the intermediate syntheses for the compounds of table 1
K) 23719, 23732, 23717, 23733, 23734
The final products were prepared from [N-(4-fluorophenyl)-5-fluoro-(indole-3-yl)acetic acids according to the following synthesis scheme and the following syntheses instructions:
Synthesis of the intermediate of compound D 23719:

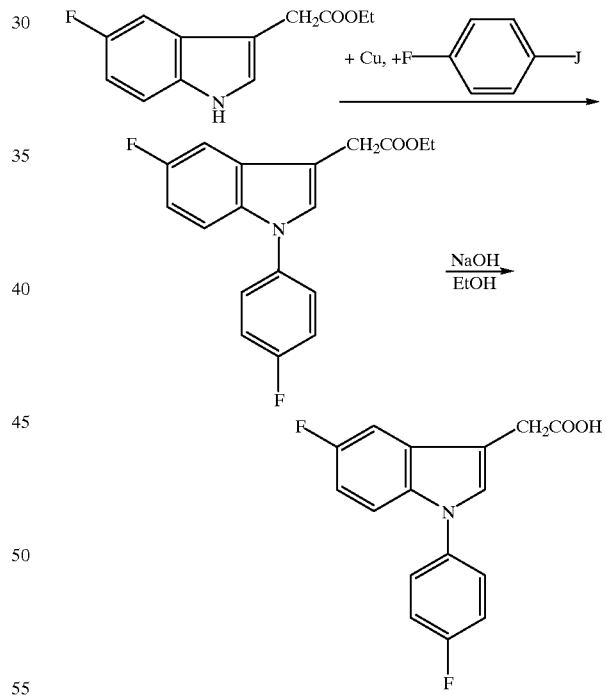

[N-($^4$-fluorophenyl)-5-fluoro-(indole-3-yl)]acetic acid ethyl ester
A mixture of 3.9 g (17.6 mMol) [5-fluoro-1H-(indole-3-yl)]acetic acid ethyl ester, 4.04 ml (35 mMol) 4-iodide-fluorobenzene, 17.6 potassium carbonate, 9.6 g copper powder and 73 ml bromobenzene are refluxed for 48 hours. The mixture is then filtered, the solvent removed under reduced pressure and the residue purified by column chromatography on silica gel with mixtures of dichloromethane/petroleum ether (4:1, v/v) to give 4.4 g of the compound as beige crystals.

Yield: 79% of theory.

[N-(4-fluorophenyl)-5-fluoro-(indole-3-yl)]acetic acid ethyl ester 4.4 g (14 mMol) [N-(4-fluorophenyl)-5-fluoro-(indole-3-yl)]acetic acid ethyl ester are dissolved in 39 ml ethanol and mixed with a solution of 1.67 g (42 mMol) NaOH in 8 ml water. The mixture is refluxed for 1 hour, the solvent removed under reduced pressure, the residue neutralised with 1n hydrochloric acid and then extracted with ethyl acetate. The organic phase is dried with sodium sulfate and the solvent is evaporated under reduced pressure. The residue is crystallized in isopropyl ether as yellow crystals.

Yield: 3.1 g (77% of theory). Melting point: 141° C.

Continuation of the intermediate syntheses for the compounds of table 1

L) 23714

The final product D-23714 is obtained from D-23720 by methylether cleavage with $BBr_3$ or NaCN in DMSO according to the following literature instructions:
a) H. Ulrich et al., J. Org. Chemistry 39, 2437 (1974)
b) J. R. McCarthy et al., Tetrahedron letters 52, 5183 (1978)
c) A. D. Fraser et al., J. Org. Chemistry 41, 170 (1976)

M) 24034

Syntheses of the intermediates of D-24034.

[N-(n-butyl)-(indole-3-yl)]acetic acid ethyl ester

A solution of 0.66 g (27.5 mMol) NaH in 200 ml DMSO is added under nitrogen atmosphere dropwise to a solution of 5.1 g commercially available (25 mMol) (indole-3-yl) acetic acid ethyl ester in 30 ml DMSO at room temperature. After 30 minutes 3.2 ml (27.6 mMol) n-butyliodide are added. The mixture is stirred for 3 hours, the reaction mixture is diluted with water and extracted with ether. After drying, the solvent is removed under reduced pressure and the residue is purified by column chromatography on silica gel. Eluting solvent: dichloromethane (petroleum ether (7:2, v/v). 4.4 g of a yellow oil are obtained.

Yield: 68% of theory.

[N-(n-butyl)-indole-3-yl)]acetic acid

The synthesis is carried out according to the saponification instructions for the primary step [N-(4-fluorophenyl)-5-fluoro-(indole-3-yl)]acetic acid ethyl ester of compound D-23719.

Yield: 96% of theory.

In addition, the compounds of the general formula 1 with G=(i) can be obtained according to the following synthesis Scheme of diagram II, wherein

W=CH

X=CH

Y=a single bond, such that the heterocyclic ring system is associated directly with the group

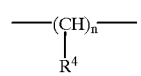

Z=2 hydrogen atoms.

DIAGRAM II

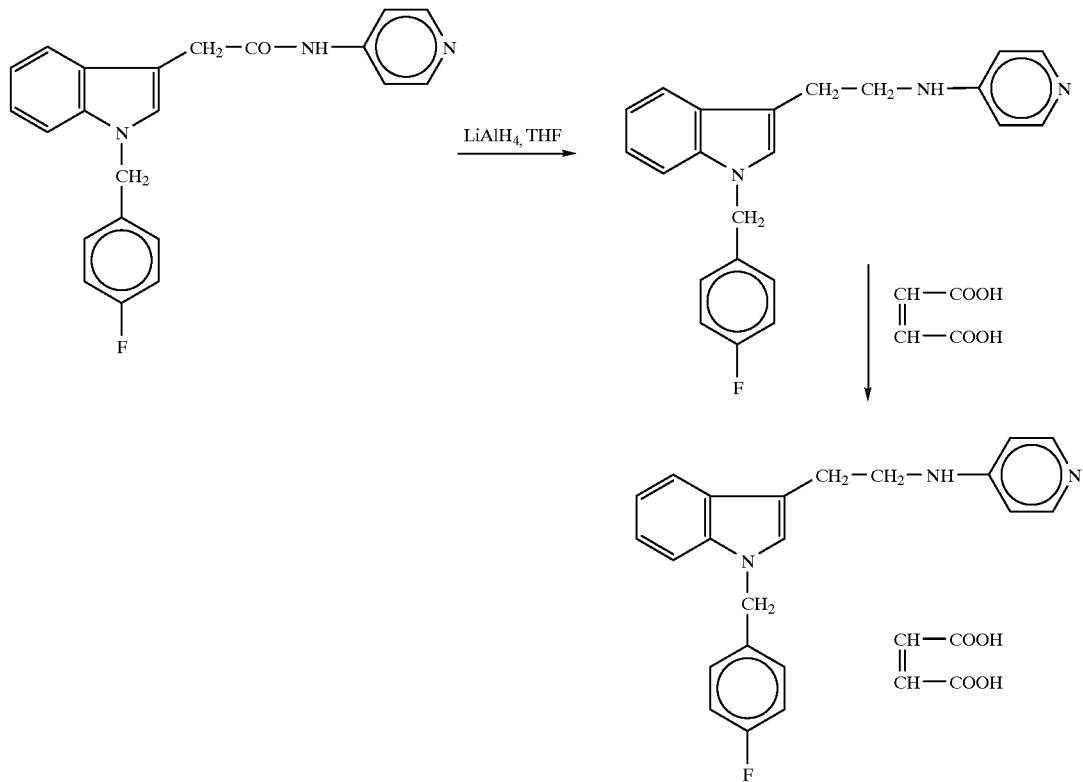

According to the above diagram II the compound N-(pyridine-3-yl)-2-[1-(4-fluorobenzyl)indole-3-yl] ethylamine maleate (D-22557) was obtained.

D-23495 was used as educt. Yield: 83% of theory related to D-23495 used. Elementary analysis:

| C | calc. | 67.67 | found | 67.62 |
|---|---|---|---|---|
| H | calc. | 5.24 | found | 5.39 |
| N | calc. | 9.1 | found | 8.92 |

According to the above diagram II the compound N-(3-pyridyl)-3-[1-methylindole-3-yl]propylamine maleate (D-22554) was obtained.
Instructions:
To a solution of 1.2 g (4.3 mMol) of the basic amide D-22684 in 150 ml anhydrous tetrahydrofuran in a three-necked flask are added a suspension of 0.8 g (21 mmol) LiAlH$_4$ in 10 ml THF under nitrogen atmosphere and vigorous stirring. The mixture is refluxed for 2 hours and cooled to 15° C. The excess LiAlH$_4$ is hydrolysed by slow addition of 10 ml iced water. The obtained mixture is extracted several times with methylene chloride, the organic phase is dried with anhydrous sodium sulfate and the solvent is removed under reduced pressure. The residue is dried and transferred to the maleate as follows:
Maleate synthesis:
The base of D-22554 obtained as set out above is dissolved in a little anhydrous ethyl acetate and mixed with a concentrated solution of maleic acid used in equivalent amount to the base in ethyl acetate, the mixture is left to stand over night at 4° C and the crystalline compound obtained—D-22554—is filtered.
MP: 118° C.; Yield: 83% of theory related to the maleate.
Elementary analysis: C calc. 66.13 found 65.92;

| C | calc. | 66.13 | found | 65.92 |
|---|---|---|---|---|
| M | calc. | 6.08 | found | 6.21 |
| N | calc. | 11.02 | found | 10.94 |

General instruction for preparing compounds of general formula 1 by analogy with diagram II The indole-3-yl carboxylic acid amide is added in a nitrogen atmosphere to a three-necked flask with stirrer, dropping funnel and reflux cooler into an anhydrous organic solvent such as diethyl ether, THF, dioxan or toluene. After adding 2–5 times, preferably 3-times the molar excess of reducing agent, such as lithium aluminium hydride, sodium cyanoborohydride or sodium borohydride/activator the mixture is heated at reflux for 1–2 hours, then cooled to approx. 10° C. and the excess reducing agent hydrolysed with excess water. The reaction mixture is extracted several times with an organic solvent, preferably methylene chloride, chloroform or also ethyl acetate, the combined extracts are dried with anhydrous sodium sulfate and then concentrated to dryness in a vacuum. The base obtained in this manner can be converted to the maleate by the following path.

The base obtained in the above manner is dissolved in an organic solvent, preferably an alcohol, such as methanol, ethanol or isopropanol or also in an aprotic solvent such as ethyl acetate or methylene chloride and treated with the equivalent amount of maleic acid which is dissolved in a little ethyl acetate or isopropanol. When left at room temperature or at 0–5° C., the corresponding maleate crystallises, is filtered and dried under reduced pressure.

According to this general instruction for the synthesis of new indole derivatives according to diagram II, the following compounds were synthesised which are listed in the following summary, quoting their code numbers (D-numbers) and the corresponding chemical designation. The following table 2 shows the structures of these compounds and their melting points from the general formula I and the substituents Y-G, W, X, $R^1$, $R^2$ and $R^3$:

| D-22551 | N-(4-pyridyl-yl)-2-(1-methylindole-3-yl)ethylamine maleate |
|---|---|
| D-22685 | N-(4-pyridyl-yl)-2-(1-benzylindole-3-yl)ethyl amine maleate |
| D-22688 | N-(4-pyridyl-yl)-4-(indole-3-yl)butylamine oxalate |
| D-22696 | N-(4-pyridyl-yl)-3-(1-methylindole-3-yl)propyl amine maleate |
| D-22697 | N-(4-pyridyl-yl)-3-(1-methylindole-3-yl)propyl amine |
| D-22554 | N-(3-pyridyl-yl)-3-(1-methylindole-3-yl)propyl-amine |
| D-22555 | N-(3-pyridyl-yl)-3-(1-benzylindole-3-yl)propyl amine |
| D-22557 | N-(3-pyridyl-yl)-2-[1-(4-fluorobenzyl)indole-3-yl]ethylamine maleate |
| D-22561 | N-(4-pyridyl-yl)-2-[1-(4-fluorobenzyl)indole-3-yl]ethylamine maleate |
| D-23699 | N-(2-(4,6-dimethylpyridyl))-2-[1-(4-fluorobenzyl)indole-3-yl]ethylamine maleate |
| D-23704 | N-(2-pyridyl-yl)-3-[1-(4-fluorobenzyl)indole-3-yl]propylamine |
| D-23710 | N-(3-pyridyl-yl)-2-(1-benzylindole-3-yl)ethyl-amine maleate |
| D-23713 | N-(2-pyridyl-yl)-2-[1-(4-fluorobenzyl)indole-3-yl]ethylamine |
| D23723 | N-(2-pyridyl-yl)-2-(1-benzylindole-3-yl)-ethylamine |
| D-24045 | N-(4-pyridyl-yl)-2-[1-butyl-indole-3-yl]ethyl-amine |
| D-24038 | N-(4-pyridyl-yl)-2-[1-(4-chlorobenzyl)indole-3-yl]ethylamine |
| D-24043 | N-(4-pyridyl-yl)-2-[1-(2-fluorobenzyl)indole-3-yl]ethylamine |
| D-24044 | N-(4-pyridyl-yl)-2-[1-(3-trifluoromethyl-benzyl)indole-3-yl]ethylamine |
| D-23709 | N-(4-pyridyl-yl)-4-[1-(4-fluorobenzyl)indole-3 yl]butylamine |
| D-22698 | N-(4-pyridyl-yl)-3-[1-(4-fluorobenzyl)indole-3 yl]propylamine |
| D-22686 | N-(3-pyridyl-yl)-3-3[1-(4-fluorobenzyl)indole-3-yl]propylamine |
| D-23731 | N-(4-pyridyl-yl)-4-(1-benzylindole-3-yl)butyl-amine |

TABLE 2

New indole compounds according to reaction diagram II

[Structure: indole-like bicyclic core with R³ at position 5, W at position 6 with R², N-R¹, X adjacent to N, and Y-G substituent at 3-position]

| D | Y—G | X | R¹ | W | R² | R³ | Fp[° C.] |
|---|---|---|---|---|---|---|---|
| 22551 (Maleat) | CH₂CH₂—NH—(4-pyridyl) | CH | CH₃ | CH | H | H | 119 |
| 22685 (Maleat) | CH₂CH₂—NH—(4-pyridyl) | CH | CH₂—C₆H₅ (benzyl) | CH | H | H | 140 |
| 22688 (Oxalat) | CH₂CH₂CH₂CH₂NH—(4-pyridyl) | CH | H | CH | H | H | 60 (deliquesce) |
| 22696 (Maleat) | CH₂CH₂CH₂NH—(4-pyridyl) | CH | CH₃ | CH | H | H | 126–128 |
| 22697 | CH₂CH₂CH₂NH—(4-pyridyl) | CH | CH₂—C₆H₅ (benzyl) | CH | H | H | oil |
| 22554 | CH₂CH₂CH₂—NH—(3-pyridyl) | CH | CH₃ | CH | H | H | 118 |
| 22555 | CH₂CH₂CH₂—NH—(3-pyridyl) | CH | CH₂—C₆H₅ (benzyl) | CH | H | H | 76 (deliquesce) |
| 22557 (Maleat) | CH₂CH₂NH—(3-pyridyl) | CH | 4-F-C₆H₄—CH₂ | CH | H | H | 142 |
| 22561 (Maleat) | CH₂CH₂NH—(4-pyridyl) | CH | 4-F-C₆H₄—CH₂ | CH | H | H | 111 |
| 23699 (Maleat) | CH₂CH₂NH—(4,6-dimethyl-2-pyridyl) | CH | 4-F-C₆H₄—CH₂ | CH | H | H | 104–105 |

TABLE 2-continued

New indole compounds according to reaction diagram II

Structure:
```
      R³
       \
        5    Y—G
        6    ‖
         \\  X
          W—N
          |  |
          R² R¹
```

| D | Y—G | X | R¹ | W | R² | R³ | Fp[° C.] |
|---|---|---|---|---|---|---|---|
| 23704 | CH₂CH₂CH₂NH—(3-pyridyl) | CH | 4-F-C₆H₄-CH₂ | CH | H | H | 112–113 |
| 23710 (Maleat) | CH₂CH₂NH—(3-pyridyl) | CH | C₆H₅-CH₂ | CH | H | H | 122–124 |
| 23713 | CH₂CH₂NH—(2-pyridyl) | CH | 4-F-C₆H₄-CH₂ | CH | H | H | 110 |
| 23723 | CH₂CH₂NH—(2-pyridyl) | CH | C₆H₅-CH₂ | CH | H | H | 116–117 |
| 24045 | CH₂CH₂NH—(4-pyridyl) | CH | CH₂CH₂CH₂CH₃ | CH | H | H | 51 (deliquesce) |
| 24038 | CH₂CH₂NH—(4-pyridyl) | CH | 4-Cl-C₆H₄-CH₂ | CH | H | H | 49 (deliquesce) |
| 24043 | CH₂CH₂NH—(4-pyridyl) | CH | 2-F-C₆H₄-CH₂ | CH | H | H | 153 |
| 24044 | CH₂CH₂NH—(4-pyridyl) | CH | 3-CF₃-C₆H₄-CH₂ | CH | H | H | oil |
| 23709 | CH₂CH₂CH₂CH₂NH—(4-pyridyl) | CH | 4-F-C₆H₄-CH₂ | CH | H | H | 80–90 |
| 22698 | CH₂CH₂CH₂NH—(4-pyridyl) | CH | 4-F-C₆H₄-CH₂ | CH | H | H | 126–128 |

TABLE 2-continued

New indole compounds according to reaction diagram II

| D | Y—G | X | R¹ | W | R² | R³ | Fp[° C.] |
|---|-----|---|----|---|----|----|----------|
| 22686 (Maleat) | CH₂CH₂CH₂—NH—[3-pyridyl] | CH | F-[phenyl]-CH₂ | CH | H | H | 136 |
| 23731 | CH₂CH₂CH₂CH₂NH—[3-pyridyl] | CH | [phenyl]-CH₂ | CH | H | H | 60–65 (deliquesce) |

Starting material for the compounds of general formula 1 which emerge from table 2 prepared according to synthesis diagram II Final synthesis products (D-compounds)intermediates of general formula 1 from table 2 (correspond to final according to synthesis diagram II products from Tab. 1)

| | |
|---|---|
| D-22554 | D-22684 |
| D-22561 | D-22558 |
| D-22555 | D-22682 |
| D-22557 | D-23495 |
| D-22685 | D-22560 |
| D-22688 | D-22552 |
| D-22696 | D-22689 |
| D-22697 | D-22683 |
| D-22698 | D-22690 |
| D-24038 | D-24035 |
| D-24043 | D-24040 |
| D-24044 | D-24041 |
| D-24045 | D-24034 |
| D-23710 | D-22680 |
| D-23699 | D-23496 |

Final synthesis products (D-compounds)intermediates of general formula 1 from table 2 (correspond to final according to synthesis diagram II products from Tab. 1)

| | |
|---|---|
| D-23713 | D-23701 |
| D-23723 | D-23725 |
| D-23709 | D-23245 |
| D-23704 | D-23728 |
| D-23731 | D-23490 |

The compounds of general formula 1 with X= C=, where a single bond of C=, which is saturated by hydrogen in formula 1 and which is linked via a methylene group to the N-atom of the group —NR⁶R⁷ of R⁵ and in the event that R⁶ and R⁷ are equal to hydrogen, this hydrogen is replaced, are obtained according to the following DIAGRAM III:

DIAGRAM III

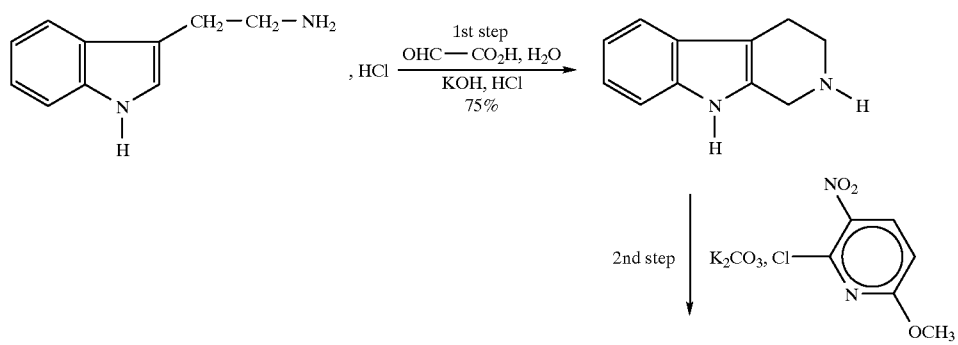

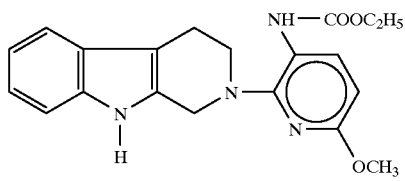 → 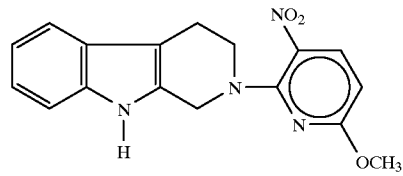

3rd step
1) NaBH₄, Pd/C, EtOH
2) Cl—COOC₂H₅
42%

The compound N-(3-ethoxycarbonylamino-6-methoxypyridine-2-yl)-1,2,3,4-tetrahydro-β-carboline-(D-22550) was obtained according to diagram III:

1st step 1,2,3,4-tetrahydro-β-carboline

In an Erlenmeyer flask 10 g (50 mMol) of tryptamine hydrochloride are dissolved with stirring at 45° C. in 160 ml $H_2O$. The mixture is cooled at room temperature and a solution of 5.3 g (56 mMol) glyoxylic acid monohydrate in 12 ml water and then, slowly, a cold solution of 2.8 g (48 mMol) KOH in 14 ml water is added. After stirring for 1 hour the precipitate formed is filtered and washed with 40 ml $H_2O$. The isolated compound is transferred to a beaker with 96 ml water. Under stirring 13.6 ml conc. hydrochloric acid is added slowly to the product. The mixture is refluxed for 30 minutes, treated again with conc. HCl and kept at boiling temperature for 15 minutes. After cooling to room temperature the precipitate is filtered, washed with 12 ml water, dissolved in 160 ml $H_2O$ and heated to approx. 55° C. under stirring. The solution is adjusted to pH 12 with 20 percent KOH. The resultant solid compound is then filtered, washed with 160 ml water and dried in vacuum.

MP: 205° C.; Yield: 75% of theory

2nd step:

N- (3-nitro-6-methoxy-2-pyridyl-yl)-1,2,3,4-tetrahydro-β-carboline 200 ml acetonitrile and 3.01 g $K_2CO_3$ are filled into a flask. The mixture is cooled with an ice-sodium chloride mixture and 2.5 g (14.5 mMol) 1,2,3,4-tetrahydro-β-carboline and 2.71 g (14.5 mMol) 2-chloro-3-nitro-6-methoxypyridine are added. This is allowed to come to room temperature with stirring and heated to reflux temperature for 2 hours. The reaction mixture is evaporated in vacuum and the residue is treated with 150 ml $H_2O$. The insoluble residue is recrystallised from ethanol.

MP: 218–220° C.; Yield: 89% of theory

3rd step:

N-(3-ethoxycarbonylamino-6-methoxypyridine-2-yl)-1,2,3,4-tetrahydro-β-carboline 4 g (12.3 mMol N-(3-nitro-6-methoxypyridine-2-yl-1,2,3,4-tetrahydro-β-carboline are added with stirring to a three-necked flask with 200 ml anhydrous ethanol. 2 g sodium borohydride and 0.5 g palladium charcoal are added under a nitrogen atmosphere. The mixture is refluxed for 2 hours with further nitrogen gassing. It is then cooled to 10° C. and 4.07 g (37 mmol) chloroformic acid ethyl ester are added dropwise. This is stirred for 2 hours at 30° C., then cooled to 15° C., filtered and concentrated. The residue is purified by column chromatography on silica gel with a mixture of petroleum ether/diisopropyl ether 50/50 (V/V). The residue recrystallised from petroleum ether/dichloromethane (95:5 (V/V)).

MP: 125° C.; Yield: 42% of theory.

General instructions for the preparation of compounds of general formula 1 according to diagram III Tryptamine hydrochloride is dissolved in water in a flask with heating. Glyoxylic acid monohydrate and a solution of an inorganic base such as NaOH, KOH, LiOH or Ba (OH)₂ are added. After the reaction the precipitate formed is filtered off and washed. The precipitate is heated in an inorganic acid such as hydrochloric acid or sulfuric acid, more conc. hydrochloric acid is added and the mixture is refluxed for some time. After cooling, the precipitate formed is filtered, washed and dissolved again in $H_2O$ with stirring. The pH is adjusted to pH 12 with 20 percent KOH and the formed 1,2,3,4-tetrahydro-β-carboline is filtered.

The 1,2,3,4-tetrahydro-β-carboline formed in this manner is heated under reflux for 1–3 hours with commercially available 2-chloro-3-nitro-6-methoxypyridine and a base, for example alkali metal carbonates or alkali hydrogen carbonates in an organic solvent, such as acetonitrile, propionitrile, THF, diethylether or dioxan. After evaporation of the solvent, the residue is diluted with water and the insoluble residue is recrystallised from ethanol.

Product obtained according to the above instructions is reduced in a manner known per se; here: N-(3-nitro-6-methoxy-pyridine-2-yl)-1,2,3,4-tetrahydro-β-carboline is dissolved in absolute ethanol and treated in a nitrogen atmosphere with sodium borohydride and Pd-C as catalyst. The mixture is refluxed for 1–4 hours. After cooling, the chloroformic acid ester is added, in this case chloroformic acid ethyl ester, and stirred for further 1–4 hours. After filtration and evaporation of the solvent the residue is purified by column chromatography on silica gel with a mixture of petroleum ether/diisopropyl ether 50:50 (V/V) and recrystallised from petroleum ether/dichloromethane.

The following examples were synthesised according to the above instructions:

N-(6-amino-5-ethoxycarbonylamino-(-2-pyridyl))-1,2,3,4-tetrahydro-β-carboline (D-22559)

MP: 191° C.; Yield: 40% of theory

Elementary analysis

| C | calc. | 64.94 | found | 65.05 |
|---|---|---|---|---|
| H | calc. | 6.02 | found | 6.01 |
| H | calc. | 19.93 | found | 19.79 |

1-methyl-N-(3-nitro-6-methoxy-(2-pyridyl))-1,2,3,4-tetrahydro-β-carboline (D-23716)

MP: 178–179° C.; Yield: 61% of theory;

1-methyl-N-(5-nitro-6-amino-(2-pyridyl))-1,2,3,4-tetrahydro-β-carboline (D-23706)

MP: 192–194° C.; Yield: 65.5% of theory

The synthesis of the intermediate 1-methyl-1,2,3,4-tetrahydro-β-carboline is carried out according to the conventional method of the Pictet-Spengler reaction from tryptamine and acetaldehyde according to the following literature:

Lit.

A. M. Jackson, A. H. Smith, Tetrahedron 24, 403 (1968) and G. Buchi, K. B. Matsumoto, H. Nishimura, J. Aver. Chem. Soc. 93, 3299 (1971):

Späth and Lederer, Chem. Ber. 63, 2101 (1930): Hahn et al. Ann. 520, 107 (1935); Chem. Ber. 71, 2163 (1938), 2192 (1938)

The compounds of general formula 1 with G=(i) can also be obtained according to the synthesis scheme of diagram IV, where:

W=CH
X=CH
Y=a single bond, in such a manner that the heterocyclic system is directly associated with the group

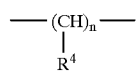

DIAGRAM IV

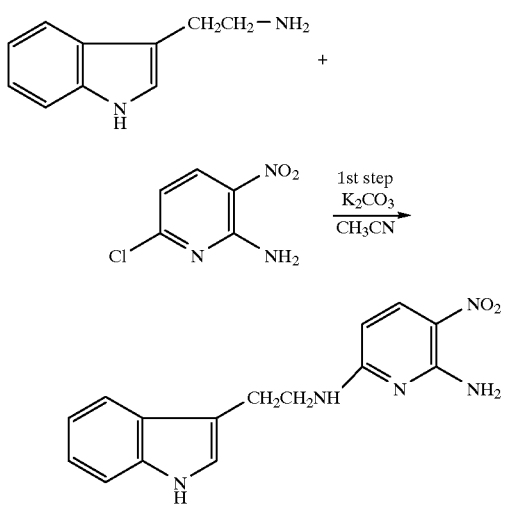

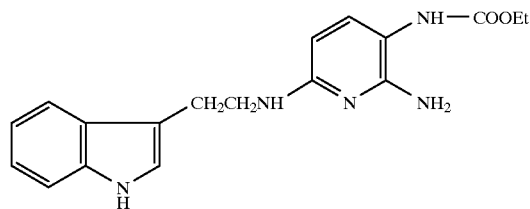

The compound N-(5-ethoxycarbonylamino-6-amino-(2-pyridyl))-2-(indole-3-yl)ethylamine (D-22191) was, for example, obtained according to the above diagram IV.

Instructions for reaction:

1st step: 3 g (18.7 mMol) tryptamine, 3.25 g (18.7 mMol) 2-amino-3-nitro-6-chloropyridine and 2.6 g $K_2CO_3$ are heated in 300 ml acetonitrile in a flask for 1 hour under reflux. The solvent is removed under reduced pressure, the residue is diluted with water and extracted with dichloromethane. The dichloromethane extracts are dried with anhydrous sodium sulfate, filtered and concentrated. The residue is purified by column chromatography on silica gel with a mixture of dichloromethane/ethanol 95:5 (V/V). and recrystallised in absol. ethanol. MP: 196° C., yield 72% of theory.

2nd step: The reduction of the nitro group and the subsequent reaction with chloroformic acid ethyl ester or chloroformic acid phenyl ester is carried out according to the general synthesis instructions to prepare compounds of general formula 1 according to diagram III (step 3) on p. 71.

Apart from acetonitrile it is also possible to use dioxan, THF, dimethylformamide and isopropanol as solvents for the 1st step. Apart from $K_2CO_3$ it is also possible to use $Na_2CO_3$, $NaHCO_3$, triethylamine or basic ion exchanges as acid catchers.

Apart from EtOH it is also possible to use methanol, isopropanol or dioxan as solvents in the 2nd step (reduction step).

In a variant of diagram IV, 2-chloro-3-nitro-6-methoxypyridine was used for the condensation with corresponding "indole-3-yl-alkylamines" (1st step) instead of 2-amino-3-nitro-6-chloropyridine, which is explained in connection with the preparation of the final compound D-23202 on the basis of the following synthesis Scheme.

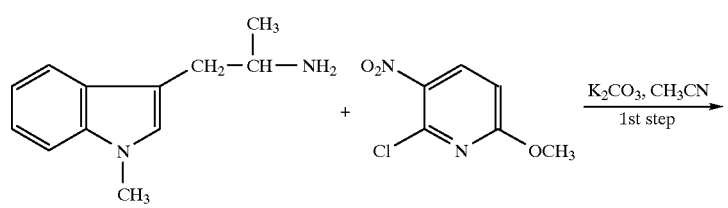

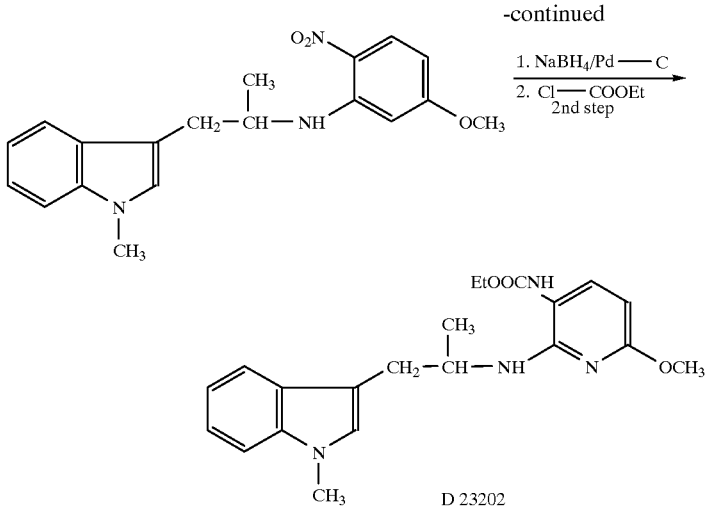

The condensation reaction of 2-(1-methylindole-3-yl) isopropylamine with 2-chloro-3-nitro-6-methoxypyridine in acetonitrile (1st step) and K$_2$CO$_3$ was carried out by analogy with the instructions on page 69 (there step 2) applying to the compound D-22550. The 2nd step with NaBH$_4$/Pd-C and the subsequent reaction with chloroformic acid ethyl ester occurred by analogy to the instructions for the synthesis of D-22550 according to step 3 therein.

According to the above general instructions for the synthesis of new indole derivatives according to diagram IV the following compounds were synthesised which are listed in the following summary, quoting their code numbers (D-numbers) and the corresponding chemical designation.

The following table 3 shows the structures of these compounds, their melting points from general formula 1 and the substituents Y-G, W, X, R$^1$, R$^2$ and R$^3$:

| | |
|---|---|
| D-22192 | N-(3-ethoxycarbonylamino-6-methoxy(2-pyridyl))-2-(indole-3-yl)ethylamine |
| D-22556 | N-(3-phenoxycarbonylamino-6-methoxy(2-pyridyl))-2-(indole-3-yl)ethylamine |
| D-22702 | N-(3-ethoxycarbonylamino-6-methoxy(2-pyridyl))--3-(indole-3-yl)propylamine |
| D-22706 | N-(3-ethoxycarbonylamino-6-methoxy(2-pyridyl))-2-(1-benzyl-indole-3-yl)isopropylamine |
| D-22948 | N-(3-ethoxycarbonylamino-6-methoxy(2-pyridyl))-2-[1-(4-fluorobenzyl-indole-3-yl)ethylamine |
| D-22949 | N-(5-ethoxycarbonylamino-6-amino(2-pyridyl))-2-[1-(4-fluorobenzyl-indole-3-yl)ethylamine maleate |
| D-22950 | N-(5-ethoxycarbonylamino-6-amino(2-pyridyl))-3-(indole-3-yl)propylamine maleate |
| D-23203 | N-(5-ethoxycarbonylamino-6-amino(2-pyridyl))-2-(1-benzylindole-3-yl)ethylamine maleate |
| D-23201 | N-(3-nitro-6-methoxy(2-pyridyl))-2-(1-benzyl-indole-3-yl)ethylamine |
| D-23205 | N-(5-ethoxycarbonylamino(2-pyridyl))-2-(1-benzylindole-3-yl)isopropylamine |
| D-23204 | N-(5-ethoxycarbonylamino-6-amino(2-pyridyl))-3-[1-(4-fluorobenzyl)indole-3-yl]propylamine |
| D-23715 | N-(5-ethoxycarbonylamino-6-amino(2-pyridyl))-2-(5-chloroindole-3-yl)ethylamine maleate |
| D-22193 | N-[1-(3-ethoxycarbonylamino-6-methoxy-(2-pyridyl))piperidine-4-yl]-3-(indole-3-yl)propionamide |
| D-22194 | N-[1-(3-ethoxycarbonylamino-6-methoxy-(2-pyridyl))-2-piperidine-4-yl](indole-3-yl)acetamide |
| D-22987 | N-(5-ethoxycarbonylamino-6-amino-(2-pyridyl))-2-(1-methylindole-3-yl)isopropylamine maleate |
| D-22988 | N-(3-ethoxycarbonylamino-6-amino-(2-pyridyl))-2-(-methylindole-3-yl)ethylamine |
| D-22989 | N-(3-ethoxycarbonylamino-6-methoxy-(2-pyridyl))-2-(5-chloroindole-3-yl)ethylamine |
| D-22990 | N-(5-ethoxycarbonylamino-6-amino-(2-pyridyl))-2-(1-methylindole-3-yl)ethylamine |
| D-22991 | N-(5-nitro-6-amino-(2-pyridyl))-2-(1-benzylindole-3-yl)ethylamine |
| D-22992 | N-(3-ethoxycarbonylamino-6-methoxy-(2-pyridyl))-2-(1-benzylindole-3-yl)ethylamine |
| D-22993 | N-(3-ethoxycarbonylamino-6-methoxy-(2-pyridyl)-3-[1-(4-fluorobenzyl)indole-3-yl)propylamine |
| D-23202 | N-(3-ethoxycarbonylamino-6-methoxy-(2-pyridyl))-2-(1-methylindole-3-yl]isopropylamine |
| D-22195 | N-[1-(5-ethoxycarbonylamino-6-amino-(2-pyridyl))-4-piperidyl]-2-(indole-3-yl)propionamide |
| D-24325 | N-[1-(5-ethoxycarbonylamino-6-amino-(2-pyridyl))-4-piperidyl](indole-3-yl]acetamide |
| D-22188 | N-(5-nitro-6amino-(2-pyridyl))-2-(indole-3-yl)ethylamine |
| D-22189 | N-[1-(5-nitro-6-amino-(2-pyridyl))-4-piperidyl]-3-(indole-3-yl)propionamide |
| D-22190 | N-[1-(5-nitro-6-amino-(2-pyridyl))-4-piperidyl]-(indole-3-yl)acetamide |
| D-22699 | N-(3-nitro-6-methoxy-(2-pyridyl))-3-(indole-3-yl)propylamine |
| D-22700 | N-(5-nitro-6-amino-(2-pyridyl))-3-(indole-3-yl)propylamine |
| D-22703 | N-(3-nitro-6-methoxy-(2-pyridyl))-2-(1-benzyl-indole-3-yl)isopropylamine |
| D-22704 | N-(3-nitro-6-methoxy-(2-pyridyl))-2-[1-(4-fluorobenzyl)indole-3-yl]ethylamine |
| D-22705 | N-(3-nitro-6-amino-(2-pyridyl))-2-[1-(4-fluoro-benzyl)indole-3-yl]ethylamine |
| D-22707 | N(5-nitro-6-amino-(2-pyridyl))-2-(1-methylindole-3-yl)isopropylamine |
| D-22984 | N-(3-nitro-6-methoxy-(2-pyridyl))-2-(1-methyl.indole-3-yl)ethylamine |
| D-22947 | N(5-nitro-6-amino-(2-pyridyl))-2-(1-methylindole-3-yl)ethylamine |
| D-22985 | N-(3-nitro-6-methoxy-(2-pyridyl))-2-(5-chloroindole-3-yl)ethylamine |
| D-22986 | N-(5-nitro-6-amino-(2-pyridyl))-2-(5-chloroindole-3-yl)ethylamine |

TABLE 3

Novel indole compounds according to reaction diagram IV

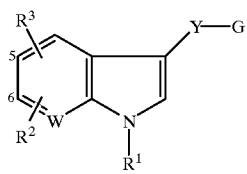

New indole derivatives according to reaction diagram IV

| D | Y—G | W | X | R¹ | R² | R³ | Fp[°C.] |
|---|---|---|---|---|---|---|---|
| 22191 | (structure: pyridine with NHCOOEt, NH₂, (CH₂)₂NH) | CH | CH | H | H | H | 46 (deliquesce) |
| 22192 | (structure: pyridine with EtOOC—HN, OCH₃, (CH₂)₂—NH) | CH | CH | H | H | H | 184 |
| 22193 | (structure: pyridine with EtOOC—HN, OCH₃, (CH₂)₂CONH-piperidine) | CH | CH | H | H | H | 92 |
| 24325 | (structure: pyridine with NCOOEt, NH₂, CH₂CON-piperidine) | CH | CH | H | H | H | 232–234 |
| 22194 | (structure: pyridine with EtOOCHN, OCH₃, CH₂CON-piperidine) | CH | CH | H | H | H | 144 |
| 22195 | (structure: pyridine with EtOOC-NH, NH₂, (CH₂)₂CON-piperidine) | CH | CH | H | H | H | 208 |
| 22556 | (structure: PhO—OC—HN pyridine with OCH₃, CH₂CH₂NH) | CH | CH | H | H | H | 131 |
| 22702 | (structure: EtOOCHN pyridine with OCH₃, (CH₂)₃NH) | CH | CH | H | H | H | 53 (deliquesce) |

TABLE 3-continued

Novel indole compounds according to reaction diagram IV

New indole derivatives according to reaction diagram IV

| D | Y—G | W | X | R$^1$ | R$^2$ | R$^3$ | Fp[°C.] |
|---|---|---|---|---|---|---|---|
| 22706 | EtOOCHN– / CH$_2$–CH(CH$_3$)–NH– pyridine –OCH$_3$ | CH | CH | CH$_2$–phenyl | H | H | 166 |
| 22948 | EtOOC—HN– / CH$_2$CH$_2$NH– pyridine –OCH$_3$ | CH | CH | CH$_2$–(4-F-phenyl) | H | H | 113 |
| 22949 | NCOOEt / (CH$_2$)$_2$NH– pyridine –NH$_2$ | CH | CH | CH$_2$–(4-F-phenyl) | H | H | 175 |
| 22950 (Maleat) | NHCOOEt / (CH$_2$)$_3$NH– pyridine –NH$_2$ | CH | CH | H | H | H | 138 |
| 22987 (Maleat) | NCOOEt / CH$_2$CH(CH$_3$)–NH– pyridine –NH$_2$ | CH | CH | CH$_3$ | H | H | 110 |
| 22988 | EtOOCHN– / (CH$_2$)NH– pyridine –OCH$_3$ | CH | CH | CH$_3$ | H | H | 120–122 |
| 22989 | EtOOCHN– / (CH$_2$)NH– pyridine –OCH$_3$ | CH | CH | H | 5-Cl | H | 90 (deliquesce) |
| 22990 (Maleat) | NCOOEt / CH$_2$CH$_2$NH– pyridine –NH$_2$ | CH | CH | CH$_3$ | H | H | 168–170 |

TABLE 3-continued

Novel indole compounds according to reaction diagram IV

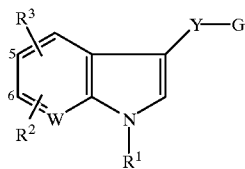

New indole derivatives according to reaction diagram IV

| D | Y—G | W | X | R¹ | R² | R³ | Fp[°C.] |
|---|---|---|---|---|---|---|---|
| 22992 | EtOOCHN-, CH₂CH₂NH- pyridine -OCH₃ | CH | CH | CH₂-phenyl | H | H | 114–116 |
| 22993 | EtOOCHN-, (CH₂)₃NH- pyridine -OCH₃ | CH | CH | CH₂-(4-F-phenyl) | H | H | 90–92 (deliquesce) |
| 23202 | EtOOCHN-, CH₂-CH(CH₃)-NH- pyridine -OCH₃ | CH | CH | CH₃ | H | H | 50 (deliquesce) |
| 23203 (Maleat) | H-NCOOEt, CH₂CH₂NH- pyridine -NH₂ | CH | CH | CH₂-phenyl | H | H | 168–170 |
| 23205 (Maleat) | H-NCOOEt, CH₂-CH(CH₃)-NH- pyridine -NH₂ | CH | CH | CH₂-phenyl | H | H | 144–146 |
| 23204 (Maleat) | H-NCOOEt, (CH₂)₃NH- pyridine -NH₂ | CH | CH | CH₂-(4-F-phenyl) | H | H | 90 (deliquesce) |
| 23715 | H-NCOOEt, (CH₂)₂NH- pyridine -NH₂ | CH | CH | H | 5-Cl | H | 182–184 |
| 22991 | NO₂, (CH₂)₂NH- pyridine -NH₂ | CH | CH | CH₂-phenyl | H | H | 158–160 |

TABLE 3-continued
Novel indole compounds according to reaction diagram IV
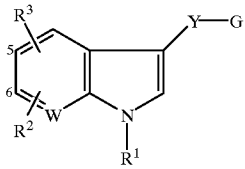
New indole derivatives according to reaction diagram IV
| D | Y—G | W | X | R¹ | R² | R³ | Fp[°C.] |
|---|---|---|---|---|---|---|---|
| 23201 | 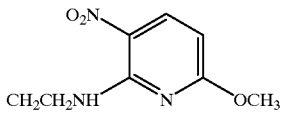 | CH | CH | 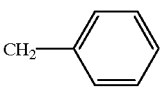 | H | H | 116–118 |
| 22188 | 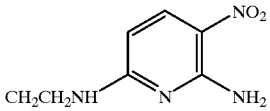 | CH | CH | H | H | H | 196 |
| 22189 | 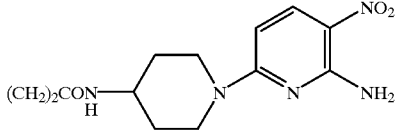 | CH | CH | H | H | H | 192 |
| 22190 | 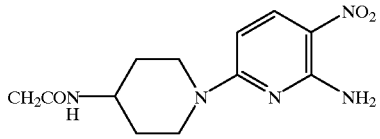 | CH | CH | H | H | H | 200 |
| 22699 | 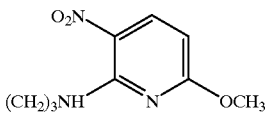 | CH | CH | H | H | H | 113 |
| 22700 | 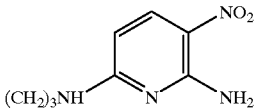 | CH | CH | H | H | H | 120 |
| 22703 | 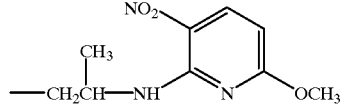 | CH | CH | 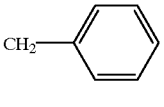 | H | H | 128 |
| 22704 | 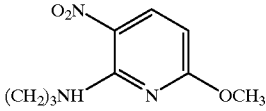 | CH | CH | 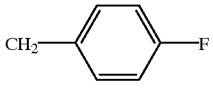 | H | H | 138 |
| 22705 | 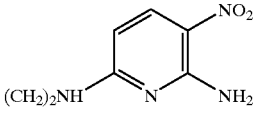 | CH | CH | 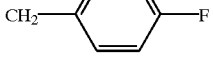 | H | H | 149 |

TABLE 3-continued

Novel indole compounds according to reaction diagram IV

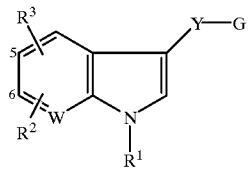

New indole derivatives according to reaction diagram IV

| D | Y—G | W | X | R¹ | R² | R³ | Fp[°C.] |
|---|---|---|---|---|---|---|---|
| 22707 | (structure: —CH₂CH(CH₃)—NH—pyridine(3-NO₂, 2-NH₂)) | CH | CH | CH₃ | H | H | 50 (deliquesce) |
| 22984 | (structure: (CH₂)₂—NH—pyridine(3-NO₂, 6-OCH₃)) | CH | CH | CH₃ | H | H | 244–246 |
| 22947 | (structure: (CH₂)₂NH—pyridine(3-NO₂, 2-NH₂)) | CH | CH | CH₃ | H | H | 140 |
| 22985 | (structure: (CH₂)₂—NH—pyridine(3-NO₂, 6-OCH₃)) | CH | CH | H | 5-Cl | H | 180–182 |
| 22986 | (structure: (CH₂)₂NH—pyridine(3-NO₂, 2-NH₂)) | CH | CH | H | 5-Cl | H | 218–220 |
| 22687 | (structure: CH₂CONH—piperidine—N—CH₂—phenyl) | CH | CH | CH₂—(4-F-phenyl) | H | H | 133 |

Starting material for the compounds of general formula 1 (intermediate synthesis) synthesised in table 3 according to reaction diagram IV:

| Final compound | Starting material [D] |
|---|---|
| D-23715 | 22986 |
| D-23203 | 22991 |
| D-22705 | 22949 |
| D-22990 | 22947 |
| D-22950 | 22700 |
| D-22987 | 22707 |
| D-22191 | 22188 |
| D-22993 | 22704 |
| D-22988 | 22984 |
| D-22556, D-22192 | 22985 |
| D-22992 | 23201 |
| D-22702 | 22699 |
| D-22195 | 22189 |
| D-24325 | 22190 |

The 2-(1-methylindole-3-yl)isopropylamine used, for example, for the final compound D-23202 can be synthesised according to the following reaction scheme:

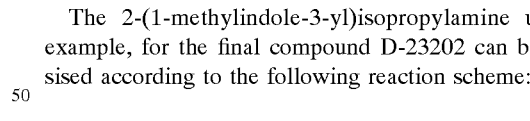

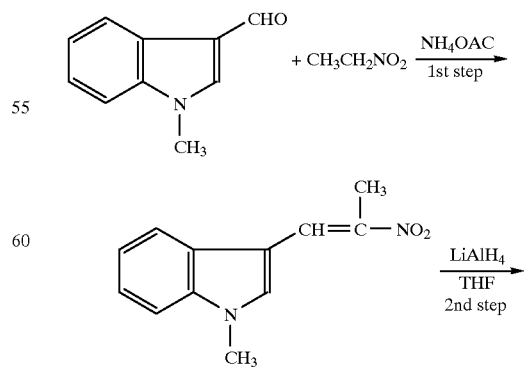

-continued

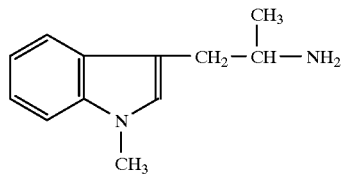

Instructions:

1st step: A solution of 9 g (56.5 mMol) 1-methyl-indole-3-carbaldehyde and 6.1 g (79 mMol) ammonium acetate in 200 ml nitroethane is refluxed with stirring for 2 hours. After substantial evaporation of the solvent an orange-coloured precipitate of 1-(1-methyl-1H-indole-3-yl)-2-nitropropene precipitates out after cooling.

Yield: 86% of theory; MP: 132–134° C.

2nd step: A suspension of 3.6 g LiAlH$_4$ in 200 ml anhydrous tetrahydrofuran (THF) is mixed dropwise with a solution of 5.4 g 1-(1-methyl-1H-indole-3-yl)-2-nitropropene in 100 ml THF. The mixture is heated to reflux for 1 hour, then cooled, excess of lithium aluminium hydride is slowly destroyed by adding 150 ml iced water and the resultant mixture is extracted with dichloromethane. The organic phase is dried with anhydrous sodium sulfate and evaporated in vacuum. A yellow oil is obtained that is dried in vacuum and immediately used for the condensation reaction with 2-chloro-3-nitro-6-methoxypyridine.

Yield: 85% of theory.

The compounds of general formula 1 from the 1H-indazole series with G=(i) can also be prepared according to the following diagram V:

DIAGRAM V:

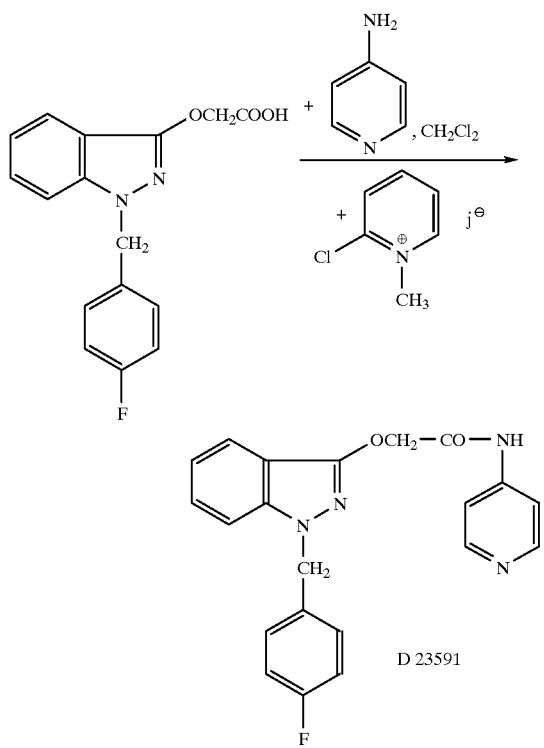

According to the above diagram V, the compound N-(4-pyridyl)-2-[1-(4-fluorobenzyl)-1H-indazole-3-yloxy]acetamide (D-23591) was for example obtained as follows:

A suspension of 1.0 g (3.33 mol) [[1-(4-fluorophenylmethyl)-1H-indazole-3-yl]oxy]-acetic acid in 20 ml methylene chloride was mixed with stirring with a suspension of 0.85 (3.33 mMol) 2-chloro-1-methylpyridinium-iodide, 1.2 ml triethylamine and 0.31 g (3.33 mMol) 4-aminopyridine in 30 ml methylene chloride and heated to reflux for 4 hours. After cooling, the reaction mixture is extracted three times with 50 ml H$_2$O and the methylene chloride solution is dried over anhydrous sodium sulfate. Evaporation the solution yields a precipitate which is purified on a silica gel column (column chromatography on silica gel with a mixture toluene (chloroform/methanol 2:1:0.5).

Yield: 0.82 g (65.4% of theory); Melting point: 136° C.–139° C.

New 1H-indazole derivatives were synthesized according to the above instructions and by analogy with the general method of procedure according to diagram I, these are listed in the following summary, quoting their code numbers (D-numbers) and the corresponding chemical designation. The following table 4 shows the structures of these compounds and their melting points from the general formula 1 and the substituents Y-G, W, X, R$^1$, R$^2$ and R$^3$:

| | |
|---|---|
| D-23557 | N-(4-pyridyl)-2-[1-(4-chlorobenzyl)-5-methoxy-1H-indazole-3-yloxy]acetamide |
| D-23590 | N-(4-pyridyl)-2-[1-(4-chlorobenzyl)-1H-indazole-3-yloxy]acetamide |
| D-23592 | N-(3-pyridyl)-2-[1-(4-chlorobenzyl)-5-methoxy-1H-indazole-3-yloxy]acetamide |
| D-23593 | N-(2-methyl-4-quinolyl)-2-[1-(4-chlorobenzyl)-5-methoxy-1H-indazole-3-yloxy]acetamide |
| D-23686 | N-(3-pyridyl)-2-[1-(4-fluorobenzyl)1H-indazole-3-yloxy]acetamide |
| D-23687 | N-(2-nitro-3-pyridyl)-2-[1-(4-fluorobenzyl)-1H-indazole-3-yloxy]acetamide |
| D-23758 | N-(3-pyridyl)-2-[1-(4-chlorobenzyl)-1H-indazole-3-yloxy]acetamide |
| D-23760 | N-(3-pyridyl)-2-[1-(4-fluorobenzyl)-5-methoxy-1H-indazole-3-yloxy]acetamide |
| D-23761 | N-(6-amino-2-pyridyl)-2-[1-(4-chlorobenzyl)-1H-indazole-3-yloxy]acetamide |
| D-23778 | N-(2-nitro-3-pyridyl)-2-[1-(4-chlorobenzyl)-1H-indazole-3-yloxy]acetamide |
| D-23779 | N-(4-pyridyl)-2-[1-(4-fluorobenzyl)-5-methoxy-1H-indazole-3-yloxy]acetamide |
| D-23781 | N-(4-pyridyl)-2-[1-(4-fluorobenzyl)-5-nitro-1H-indazole-3-yloxy]acetamide |
| D-23782 | N-(5-methoxycarbonyl-2-pyridyl)-2-[1-(4-fluorobenzyl)-1H-indazole-3-yloxy]acetamide |
| D-23783 | N-(6-amino-2-pyridyl)-2-[1-(4-fluorobenzyl-indazole-3-yloxy]acetamide |
| D-23828 | N-(4-pyridyl)-2-[1-(4-chlorobenzyl)-5-nitro-1H-indazole-3-yloxy]acetamide |
| D-23829 | N-(6-amino-2-pyridyl)-2-[1-(4-chlorobenzyl)-5-methoxy-1H-indazole-3-yloxy]acetamide |
| D-23830 | N-(5-methoxycarbonyl-2-pyridyl)-2-[1-(4-fluorobenzyl-5-methoxy-1H-indazole-3-yloxy]acetamide |
| D-23861 | N-(6-amino-2-pyridyl)-2-[1-(4-fluorobenzyl)-5-methoxy-1H-indazole-3-yloxy]acetamide |
| D-23874 | N-(5-methoxycarbonyl-2-pyridyl)-2-[1-(4-chlorobenzyl-5-methoxy-1H-indazole-3-yloxy]acetamide |
| D-23915 | N-(2-nitro-3-pyridyl)-2-[1-(4-fluorobenzyl)-5-methoxy-1H-indazole-3-yloxy]acetamide |
| D-23930 | N-(5-methoxycarbonyl-2-pyridyl)-2-[1-(4-chlorobenzyl-1H-indazole-3-yloxy]acetamide |

TABLE 4

Novel 1H-indazole derivatives according to diagram V

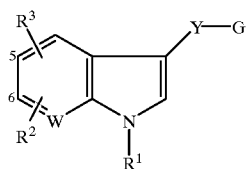

Formula 1

| D | —Y—G | R¹ | X | W | R³ | R² | Fp. |
|---|---|---|---|---|---|---|---|
| 23557 | O-CH₂-C(=O)-NH-(4-pyridyl) | CH₂-(4-Cl-phenyl) | N | CH | H | 5-O—CH₃ | 97–99° C. |
| 23590 | O-CH₂-C(=O)-NH-(4-pyridyl) | CH₂-(4-Cl-phenyl) | N | CH | H | H | 158–161° C. |
| 23591 | O-CH₂-C(=O)-NH-(4-pyridyl) | CH₂-(4-F-phenyl) | N | CH | H | H | 136–139° C. |
| 23592 | O-CH₂-C(=O)-NH-(3-pyridyl) | CH₂-(4-Cl-phenyl) | N | CH | H | 5-O—CH₃ | 177–178° C. |
| 23593 | O-CH₂-C(=O)-NH-(2-methyl-4-quinolyl) | CH₂-(4-Cl-phenyl) | N | CH | H | 5-O—CH₃ | 152–160° C. |
| 23686 | O-CH₂-C(=O)-NH-(3-pyridyl) | CH₂-(4-F-phenyl) | N | CH | H | H | Öl |
| 23687 | O-CH₂-C(=O)-NH-(2-nitro-3-pyridyl) | CH₂-(4-F-phenyl) | N | CH | H | H | 158–160° C. |
| 23758 | O-CH₂-C(=O)-NH-(3-pyridyl) | CH₂-(4-Cl-phenyl) | N | CH | H | H | 148–150° C. |

TABLE 4-continued
Novel 1H-indazole derivatives according to diagram V
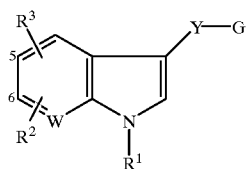
Formula 1
| D | —Y—G | R¹ | X | W | R³ | R² | Fp. |
|---|---|---|---|---|---|---|---|
| 23760 | -NH-3-pyridyl) | CH2-C6H4-4-F | N | CH | H | 5-O—CH3 | 159–160° C. |
| 23761 | -NH-(6-amino-pyridin-2-yl)) | CH2-C6H4-4-Cl | N | CH | H | H | 170–171° C. |
| 23778 | -NH-(2-nitro-pyridin-3-yl)) | CH2-C6H4-4-Cl | N | CH | H | H | 154–156° C. |
| 23779 | -NH-4-pyridyl) | CH2-C6H4-4-F | N | CH | H | 5-O—CH3 | 157–158° C. |
| 23781 | -NH-4-pyridyl) | CH2-C6H4-4-F | N | CH | H | 5-NO2 | 176–178° C. |
| 23782 | -NH-(5-methoxycarbonyl-pyridin-2-yl)) | CH2-C6H4-4-F | N | CH | H | H | 160.5–161.5° |
| 23783 | -NH-(6-amino-pyridin-2-yl)) | CH2-C6H4-4-F | N | CH | H | H | 193.5–194.5° |
| 23828 | -NH-4-pyridyl) | CH2-C6H4-4-Cl | N | CH | H | 5-NO2 | 207.5–208° C. |

TABLE 4-continued

Novel 1H-indazole derivatives according to diagram V

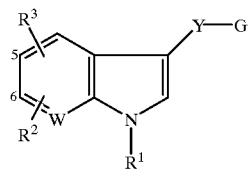

Formula 1

| D | —Y—G | R¹ | X | W | R³ | R² | Fp. |
|---|---|---|---|---|---|---|---|
| 23829 | O-CH₂-C(=O)-NH-(pyridin-2-yl)-6-NH₂ | CH₂—C₆H₄—Cl (4-Cl) | N | CH | H | 5-O—CH₃ | 178–180° C. |
| 23830 | O-CH₂-C(=O)-NH-(pyridin-2-yl)-5-C(=O)OCH₃ | CH₂—C₆H₄—F (4-F) | N | CH | H | 5-O—CH₃ | 160–160.5° C. |
| 23861 | O-CH₂-C(=O)-NH-(pyridin-2-yl)-6-NH₂ | CH₂—C₆H₄—F (4-F) | N | CH | H | 5-O—CH₃ | 157.5–158° C. |
| 23874 | O-CH₂-C(=O)-NH-(pyridin-2-yl)-5-C(=O)OCH₃ | CH₂—C₆H₄—Cl (4-Cl) | N | CH | H | 5-O—CH₃ | 159–160° C. |
| 23915 | O-CH₂-C(=O)-NH-(pyridin-3-yl)-2-NO₂ | CH₂—C₆H₄—F (4-F) | N | CH | H | 5-O—CH₃ | 180–181° C. |
| 23930 | O-CH₂-C(=O)-NH-(pyridin-2-yl)-5-C(=O)OCH₃ | CH₂—C₆H₄—Cl (4-Cl) | N | CH | H | H | 169–170° C. |

Starting compounds for reactions according to diagram V

The starting substances according to the reactions described for diagram V can be prepared from the 1-benzyl-1H-indazole-3-ols published by L. Baiochchi et al. Synthesis 1978, 633 and thus known to the literature by reaction with chloroacetic acid ethyl ester in DMF with $K_2CO_3$ and also in aqueous sodium hydroxide solution at room temperature or elevated temperature up to 80° C. The (1-benzyl-1H-indazole-3-yl)oxyacetic acid ethyl esters primarily formed thereby are reacted with sodium hydroxide solution at 50° C. in an ethanol/water solvent mixture and the corresponding (1-benzyl-1H-indazole-3-yl)oxyacetic acids precipitated out by acidulation with dilute hydrochloric acid.

In addition, the compounds of general formula 1 with G=(ii) can be obtained according to the synthesis path of diagram VI, where

W=CH
X=N
Y=O

DIAGRAM VI

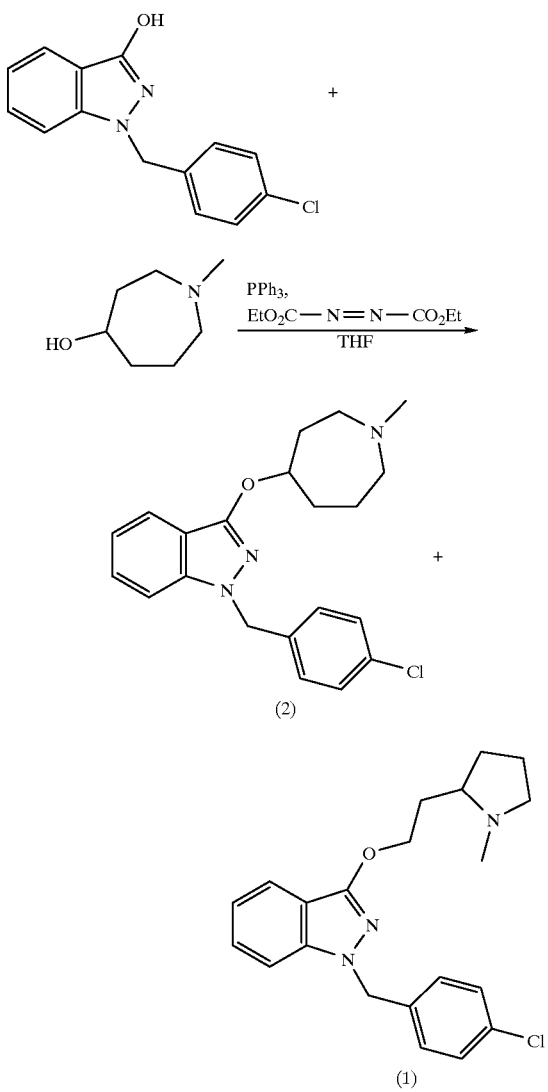

(2)

(1)

The compounds 1-(4-chlorobenzyl)-3-[2-(1-methylpyrrolidine-2-yl)-ethoxy]-1H-indazole (D-22591) and 1-(4-chlorobenzyl)-3-(1-methyl-azepan-4-yloxy)-1H-indazole (D-22175) were obtained according to the above diagram VI:

Instructions:
4,1-(4-chlorobenzyl)-3-[2-(1-methylpyrrolidine-2-yl)-ethoxy]-1H-indazole(1) and 1-(4-chlorobenzyl)-3-(1-methyl-azepan-4-yloxy)-1H-indazole (2)

A solution of 3.75 g (29 mMol) 1-methylazepan-4-ol in 15 ml anhydrous THF was added dropwise to a solution of 5 g (19 mMol) 1-(4-chlorobenzyl)-1H-indazole-3-one in 150 ml anhyclrous THF at 23° C. with stirring. After stirring for approx. 10 min. at room temperature 7.6 g (29 mMol) triphenylphosphine and a solution of 5.1 g (29 mMol) azodicarboxylic acid ethyl ester in 10 ml anhydrous THF was then immediately added dropwise. After stirring for 5 hours at room temperature the solvent was removed at reduced pressure. The residue was purified by flash chromatography in the first with a mixture of $CH_2Cl_2$/aceton (80:20), whereby triphenylphosphine oxide and small amounts of unreacted 1-(4-chlorobenzyl)-1H-indazole-3-one were eluted. Elution with a mixture of $CH_2Cl_2$/methanol (80:20) yielded a mixture consisting of the two title compounds 1 and 2: 1-(4-chlorobenzyl)-3-[2-(1-methylpyrrolidine-2-yl)-ethoxy]-1H-indazole (1) and 1-(4-chlorobenzyl)-3-[(1-methylazepan-4-yl)oxy]-1H-indazole (2).

Structure and elementary analysis of (1) (D-22591)

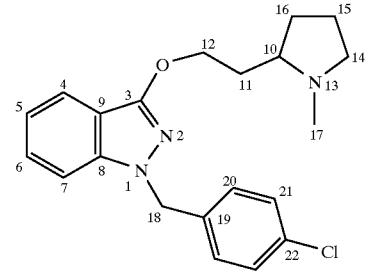

$C_{21}H_{24}N_3OCl$ [369.9]: calc.:  C 68.19% H 6.54% N 11.36%
found: C 67.95% H 6.33% N 11.15%

Structure and elementary analysis of (2) (D-22175)

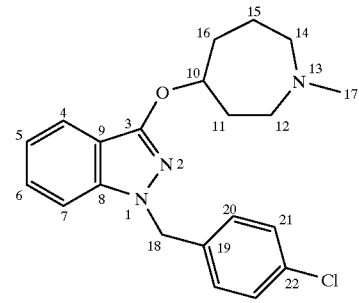

$C_{21}H_{24}N_3OCl$ [369.9]: calc.:  C 68.19% H 6.54% N 11.36%
found: C 68.09% H 6.50% N 11.10%

General instructions for the preparation of compounds of general formula 1 for G=(ii)

A solution of the amine is added dropwise at room temperature to a stirred solution of the indazole derivative in an organic solvent, such as THF, dioxan, DMF or DMA. This mixture is briefly stirred before adding triphenylphosphine and azodicarboxylic acid ester in THF. After the end of the reaction the solvent is removed under reduced pressure. The residue is purified by column chromatography with a mixture of methylene chloride/acetone (80:20).

The following compounds were synthesized according to the above instructions for the synthesis of novel indazole derivatives according to diagram VI and according to the example set out as well as to the General Instructions, these are set out in the following summary, quoting their code numbers (D-numbers) and the corresponding chemical designation. The following table 5 shows the structures of these compounds and their melting points from the general formula 1 and the substituents Y-G, W, X, $R^1$, $R^2$, $R^3$:

| D | | |
|---|---|---|
| D-21963 | 1-(4-fluorobenzyl)-3-(1-methylazepan-4-yloxy)-1H-indazole | |
| D-22055 | 1-[(4-fluorobenzyl)-3-(1-methyl-4-piperidyloxy)-1H-indazole | |
| D-22105 | 1-(4-chlorobenzyl)-3-(1-methyl-4-piperidyloxy)-1H-indazole | |
| D-23172 | 1-(4-chlorobenzyl)-3-[2-(1-methylpyrrolidine-2-yl)-ethoxy]-5-nitro-1H-indazole | |
| D-23173 | 1-(4-chlorobenzyl)-3-(1-methylazepan-4-yloxy)-5-nitro-1H-indazole | |
| D-22453 | 1-(4-fluorobenzyl)-3-[3-(N-diethyl amino)-propoxy]-1H-indazole | |
| D-22470 | 1-(3-pyridylmethyl)-3-[3-(N-diethylamino)-propoxy]-1H-indazole | |
| D-22585 | 1-(4-fluorobenzyl)-3-[3-(N-dimethylamino)-propoxy]-1H-indazole hydrochloride | |
| D-22627 | 1-(2-quinolylmethyl)-3-[3-(N-dimethylamino)-propoxy]-1H-indazole | |
| D-22634 | 1-(2-quinolylmethyl)-3-[3-(N-dimethylamino)-propoxy]-1H-indazole hydrochloride | |
| D-22768 | 1-(4-fluorobenzyl)-3-[3-(N-dimethylamino)-propoxy]-1H-indazole maleate | |
| D-22814 | 1-(4-chlorobenzyl)-3-[3-(N-dimethylamino)-propoxy]-1H-indazole | |
| D-22890 | 1-(4-chlorobenzyl)-3-[3-N-diethylamino)-propoxy]-5-nitro-1H-indazole hydrochloride | |
| D-22895 | 1-(4-chlorobenzyl)-3-[3-(N-diethylamino)-propoxy]-1H-indazole | |
| D-22952 | 1-(4-chlorobenzyl)-3-[3-(N-diethylamino)-propoxy]-5-[(4-methoxyphenyl)-methylcarbonylamino]-1H-indazole hydrochloride | |
| D-22953 | 1-(4-chlorobenzyl)-3-[3-(N-diethylamino)-propoxy]-5-[(4-methoxyphenyl)-carbonylamino]-1H-indazole hydrochloride | |
| D-22954 | 1-(4-chlorobenzyl)-3-[3-(N-diethylamino)-propoxy)-5-[(4-bromophenoxy)-carbonylamino]-1H-indazole hydrochloride | |
| D-23097 | 1-(4-fluorobenzyl)-3-[3-(N-diethylamino)-propoxy]-5-(ethoxycarbonylamino)-1H-indazole hydrochloride | |
| D-23174 | 1-(4-fluorobenzyl)-3-(3-(N-dimethylamino)-propoxy]-5-nitro-1H-indazole hydrochloride | |
| D-23225 | 1-(4-chlorobenzyl)-3-[3-(N-diethylamino)-propoxy)-5-(cyclohexyloxycarbonylamino]-1H-indazole hydrochloride | |
| D-23236 | 1-(4-fluorobenzyl)-3-[3-(N-diethylamino)-propoxy]-5-(cyclohexyloxycarbonylamino)-1H-indazole hydrochloride | |
| D-23308 | 1-(4-fluorobenzyl)-3-[3-N-dimethylamino)-propoxy]-5-methoxy-1H-indazole | |
| D-23309 | 1-(4-chlorobenzyl)-3-(3-(N-diethylamino)-propoxyl-5-(ethoxycarbonylamino)-1H-indazole hydrochloride | |
| D-23517 | 1-(4-fluorobenzyl)-3-[3-(N-diethylamino)-propoxy]-5-(fluoroenylmethyloxycarbonylamino)-1H-indazole hydrochloride | |
| D-23584 | 1-(4-fluorobenzyl)-3-[3-(N-diethylamino)-propoxy]-5-(cyclopentyloxycarbonylamino)-1H-indazole hydrochloride | |

TABLE 5

Novel indazole derivatives according to diagram VI

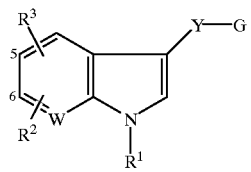

Formula 1

| D | —Y—G | R¹ | X | W | R³ | R² | Fp. |
|---|---|---|---|---|---|---|---|
| 21963 | (1-methylazepan-4-yloxy structure) | CH₂-(4-F-phenyl) | N | CH | H | H | oil |
| 22055 | (1-methyl-4-piperidyloxy structure) HCl | CH₂-(4-F-phenyl) | N | CH | H | H | 140–144° C. |
| 22105 | (1-methyl-4-piperidyloxy structure) | CH₂-(4-Cl-phenyl) | N | CH | H | H | 82° C. |

TABLE 5-continued

Novel indazole derivatives according to diagram VI

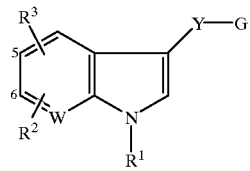

Formula 1

| D | —Y—G | R¹ | X | W | R³ | R² | Fp. |
|---|---|---|---|---|---|---|---|
| 23173 | (1-methyl-azepan-4-yl)oxy | CH₂-(4-Cl-C₆H₄) | N | CH | H | 5-NO₂ | 75–78° C. |
| 23172 | 2-(1-methyl-pyrrolidin-2-yl)ethoxy | CH₂-(4-Cl-C₆H₄) | N | CH | H | 5-NO₂ | 171–174° C. |
| 22175 | (1-methyl-azepan-4-yl)oxy | CH₂-(4-Cl-C₆H₄) | N | CH | H | H | oil |
| 22591 | 2-(1-methyl-pyrrolidin-2-yl)ethoxy | CH₂-(4-Cl-C₆H₄) | N | CH | H | H | oil |
| 22453 | 3-(diethylamino)propoxy | CH₂-(4-F-C₆H₄) | N | CH | H | H | 102° C. |
| 22470 | 3-(diethylamino)propoxy | CH₂-(pyridin-3-yl) | N | CH | H | H | oil |
| 22585 | 3-(dimethylamino)propoxy · HCl | CH₂-(4-F-C₆H₄) | N | CH | H | H | 103° C. |
| 22768 | 3-(dimethylamino)propoxy · Maleat | CH₂-(4-F-C₆H₄) | N | CH | H | H | 85° C. |
| 22814 | 3-(dimethylamino)propoxy | CH₂-(4-Cl-C₆H₄) | N | CH | H | H | oil |
| 22890 | 3-(diethylamino)propoxy · HCl | CH₂-(4-Cl-C₆H₄) | N | CH | H | 5-NO₂ | 134–138° C. |

TABLE 5-continued

Novel indazole derivatives according to diagram VI

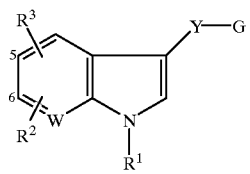

Formula 1

| D | —Y—G | R¹ | X | W | R³ | R² | Fp. |
|---|---|---|---|---|---|---|---|
| 22895 | O-CH₂CH₂CH₂-N(CH₂CH₃)₂ | CH₂-C₆H₄-Cl (4-) | N | CH | H | H | oil |
| 22952 | O-CH₂CH₂CH₂-N(CH₂CH₃)₂ · HCl | CH₂-C₆H₄-Cl (4-) | N | CH | H | 5-NH-CO-CH₂-C₆H₄-OCH₃ (4-) | 147–149° C. |
| 22953 | O-CH₂CH₂CH₂-N(CH₂CH₃)₂ · HCl | CH₂-C₆H₄-Cl (4-) | N | CH | H | 5-NH-CO-CH₂-C₆H₄-OCH₃ (4-) | 170–172° C. |
| 22954 | O-CH₂CH₂CH₂-N(CH₂CH₃)₂ · HCl | CH₂-C₆H₄-Cl (4-) | N | CH | H | 5-NH-CO-O-C₆H₄-Br (4-) | 178–180° C. |
| 23097 | O-CH₂CH₂CH₂-N(CH₂CH₃)₂ · HCl | CH₂-C₆H₄-F (4-) | N | CH | H | 5-NH-CO-O-CH₂CH₃ | 99–102° C. |
| 22627 | O-CH₂CH₂CH₂-N(CH₂CH₃)₂ · HCl | | N | CH | H | H | 175° C. |
| 22634 | O-CH₂CH₂CH₂-N(CH₃)₂ · HCl | | N | CH | H | H | 152° C. |
| 23174 | O-CH₂CH₂CH₂-N(CH₂CH₃)₂ · HCl | CH₂-C₆H₄-F (4-) | N | CH | H | 5-NO₂ | 150–153° C. |
| 23225 | O-CH₂CH₂CH₂-N(CH₂CH₃)₂ · HCl | CH₂-C₆H₄-Cl (4-) | N | CH | H | 5-NH-CO-O-cyclohexyl | 181° C. |
| 23236 | O-CH₂CH₂CH₂-N(CH₂CH₃)₂ · HCl | CH₂-C₆H₄-F (4-) | N | CH | H | 5-NH-CO-O-cyclohexyl | 159° C. |

TABLE 5-continued

Novel indazole derivatives according to diagram VI

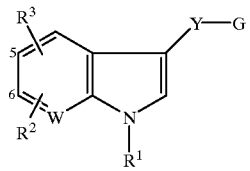

Formula 1

| D | —Y—G | R¹ | X | W | R³ | R² | Fp. |
|---|---|---|---|---|---|---|---|
| 23308 | CH₂CH₂CH₂O—) | CH₂—C₆H₄—F | N | CH | H | 5-O—CH₃ | 89° C. |
| 23309 | CH₂CH₂CH₂O—) HCl | CH₂—C₆H₄—Cl | N | CH | H | 5-NH—C(O)—O—CH₂CH₃ | 95° C. |
| 23517 | CH₂CH₂CH₂O—) HCl | CH₂—C₆H₄—F | N | CH | H | 5-NH—C(O)—O—CH₂-fluorenyl | 142° C. |
| 23584 | CH₂CH₂CH₂O—) HCl | CH₂—C₆H₄—F | N | CH | H | 5-NH—C(O)—O-cyclopentyl | oil |

What is claimed is:

1. A compound of formula 1:

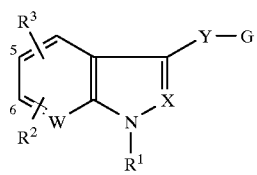

Formula 1 wherein

R¹ represents hydrogen, a straight-chained (C₁–C₆)alkyl group, which is optionally substituted by phenyl or halogen-substituted phenyl;

R² represents hydrogen or a branched (C₁–C₆) alkyl group;

R³ represents hydrogen;

W represents CH;

X represents CH;

Y represents a single bond in such a manner that the heterocyclic system is directly associated with the group

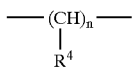

wherein n is 1–6 and R⁴ represents hydrogen; G represents

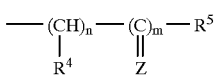

wherein m is 1, Z represents O or two hydrogen atoms, R⁵ represents the radical

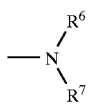

wherein R⁶ represents hydrogen and R⁷ represents a pyridine skeleton, which is linked to one of the ring carbon atoms and is optionally substituted with radicals R⁸ and R⁹ which may be identical or different and represent straight-chained (C₁–C₆) alkyl, (C₁–C₆)alkoxy, or ethoxycarbonylamino, and wherein

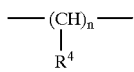

may also include one —CH=CH— unit when n is equal to or greater than two;

and pharmaceutically usable acid addition salts thereof.

2. N-(4-pyridyl)-[1-(4-fluorobenzyl)indole-3-yl]acetamine and the physiologically acceptable acid addition salts thereof.

3. N-(3-pyridyl)-2-[1-(4-fluorobenzyl)indole-3-yl]ethylamine and the physiologically acceptable acid addition salts thereof.

4. N-(4-pyridyl)-2-(1-benzyl-2-methyl-5-isopropylindole-3-yl)acetamide, and the physiologically acceptable acid addition salts thereof.

5. N-(4-pyridyl)-2-(5-isopropyl-1H-indole-3-yl)acetamine and the physiologically acceptable acid addition salts thereof.

6. N-(2-pyridyl)-2-[1-(4-fluorobenzyl)indole-3-yl]ethylamine, and the physiologically acceptable acid addition salts thereof.

7. N-(4-pyridyl)-2-[1-(4-fluorobenzyl)6-hydroxyindole-3-yl]acetamide, and the physiologically acceptable acid addition salts thereof.

8. N-(4,6-dimethyl-2-pyridyl)-3-[1-(4-fluorobenzyl)indole-3-yl)]propenamide and the physiologically acceptable acid addition salts thereof.

9. N-(4-pyridyl)-2-(1-benzylindole-3-yl)ethylamine and the physiologically acceptable acid addition salts thereof.

10. N-(3-pyridyl)-3-[1-(4-fluorobenzyl)-indole-3-yl)propylamine and the physiologically acceptable acid addition salts thereof.

11. N-(4-pyridyl)-3-(1-p-fluorobenzylindole-3-yl)propylamine and the physiologically acceptable acid addition salts thereof.

12. N-(4-pyridyl)-3-(1-methylindole-3-yl)propylamine and the physiologically acceptable acid addition salts thereof.

13. N-(4-pyridyl)-2-[1-(4-fluorobenzyl)indole-3-yl]ethylamine and the physiologically acceptable acid addition salts thereof.

14. N-(4-pyridyl)-(1-ethylindole-3-yl)acetamide and the physiologically acceptable acid addition salts thereof.

15. N-(3-ethoxycarbonylamino-6-methoxy-2-pyridyl)-2-(1-benzylindole-3-yl)ethylamine and the physiologically acceptable acid addition salts thereof.

16. N-(3-ethoxycarbonylamino-6-methoxy-2-pyridyl)-3-(1-(4-fluorobenzyl)indole-3-yl)propylamine and the physiologically acceptable acid addition salts thereof.

17. A medicament comprising a compound according to one of claims 2, 3, 5–8 or 1 and a physiologically acceptable carrier, diluting agent or auxiliary substance.

* * * * *